(12) United States Patent
Parker et al.

(10) Patent No.: US 7,892,501 B2
(45) Date of Patent: Feb. 22, 2011

(54) AIR SANITIZER

(75) Inventors: Andrew J. Parker, Novato, CA (US); Gregory S. Snyder, San Rafael, CA (US)

(73) Assignee: Sharper Image Acquisition LLC, New York, NY (US)

( * ) Notice: Subject to any disclaimer, the term of this patent is extended or adjusted under 35 U.S.C. 154(b) by 1152 days.

(21) Appl. No.: 11/293,538

(22) Filed: Dec. 2, 2005

(65) Prior Publication Data

US 2006/0159594 A1 Jul. 20, 2006

Related U.S. Application Data

(63) Continuation-in-part of application No. 11/004,397, filed on Dec. 3, 2004.

(60) Provisional application No. 60/590,445, filed on Jul. 23, 2004.

(51) Int. Cl.
*B01J 19/08* (2006.01)
(52) U.S. Cl. ............... 422/186.04; 422/121; 422/186.3
(58) Field of Classification Search ............... 422/121, 422/186.3, 186.04
See application file for complete search history.

(56) References Cited

U.S. PATENT DOCUMENTS

| | | | |
|---|---|---|---|
| 2,247,409 A | 7/1941 | Roper | |
| 3,374,941 A | 3/1968 | Okress | |
| 5,565,685 A | 10/1996 | Czako et al. | |
| 5,702,507 A | 12/1997 | Wang | |
| 5,874,701 A * | 2/1999 | Watanabe et al. | 204/157.15 |
| 6,497,840 B1 | 12/2002 | Palestro et al. | |
| 6,544,485 B1 * | 4/2003 | Taylor | 422/186.04 |
| 6,680,028 B1 | 1/2004 | Harris | |
| 2002/0098109 A1 * | 7/2002 | Nelson et al. | 422/5 |
| 2003/0206840 A1 * | 11/2003 | Taylor et al. | 422/186.04 |

FOREIGN PATENT DOCUMENTS

JP 2003-303651 * 10/2003

OTHER PUBLICATIONS

English abstract for JP 2003-303651, inventor: Watanabe, published: Oct. 2003.*
PCT International Search Report.

* cited by examiner

*Primary Examiner*—Sean E Conley
(74) *Attorney, Agent, or Firm*—Arent Fox LLP

(57) ABSTRACT

A germicidal lamp can selectively direct germicidal light emitted within an air transporting and/or conditioning system. The system can include a housing, an emitter electrode configured within the housing, and a collector electrode configured within the housing and located downstream from the emitter electrode. The system can further include a driver electrode that can be removed from the housing through a side portion of the housing. The driver electrode can be insulated with a dielectric material and/or a catalyst. A removable trailing electrode can be configured within the housing and located downstream from the collector electrode. A first voltage source can be electrically coupled to the emitter electrode and the collector electrode, and a second voltage source can be electrically coupled to the trailing electrode. The second voltage source can be independently and selectively controllable from the first voltage source.

21 Claims, 14 Drawing Sheets

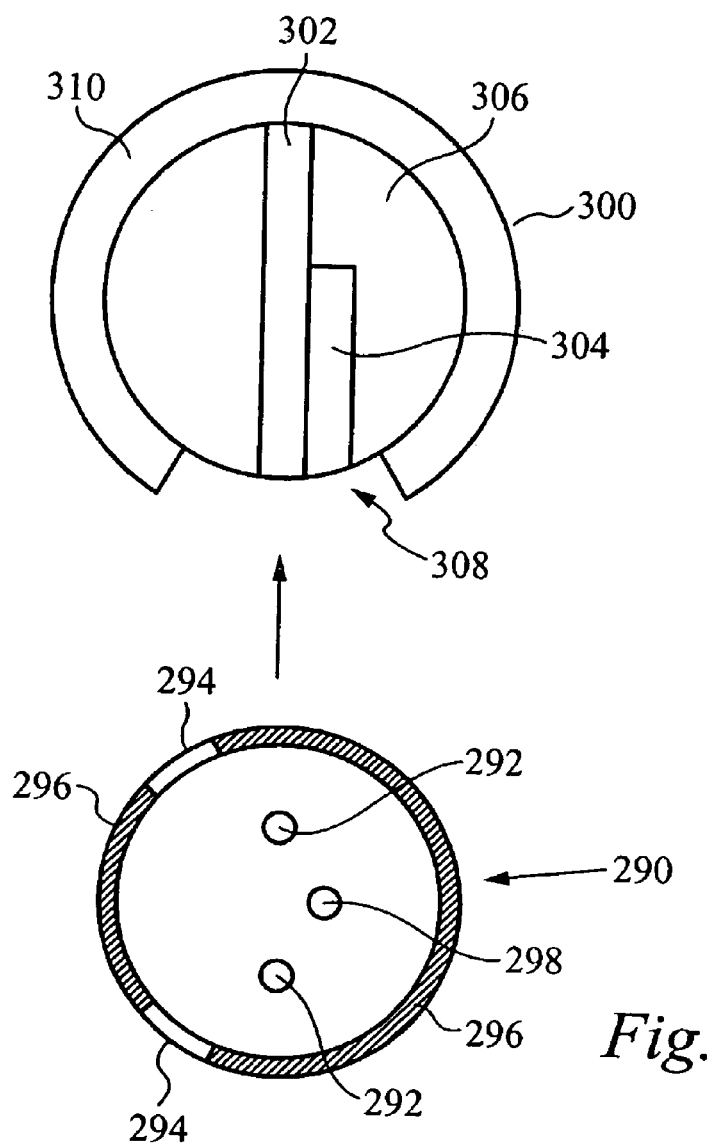
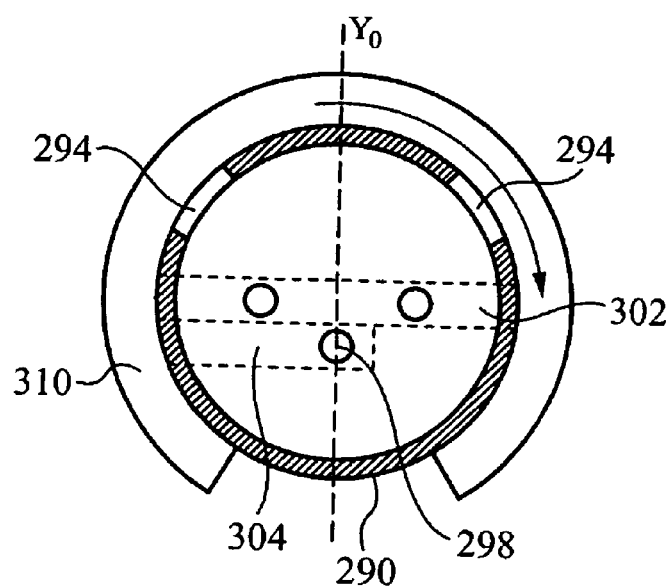
Fig. 12A
Fig. 12B

AIR SANITIZER

This application is a continuation-in-part of application Ser. No. 11/004,397, filed on Dec. 3, 2004, and claims benefit of priority to a provisional application No. 60/590,445, filed on Jul. 23, 2004, both of which are incorporated by reference herein in entirety.

BACKGROUND

The use of an electric motor to rotate a fan blade to create an airflow has long been known in the art. Such fans can produce substantial airflow (e.g., 1,000 ft$^3$/minute or more), however, essentially no sanitizing of the flowing air occurs.

It is known to provide such fans with a HEPA-compliant filter element to remove particulate matter larger than perhaps 0.3 p.m. Unfortunately, the resistance to airflow presented by the filter element may require doubling the electric motor size to maintain a desired level of airflow. Further, HEPA-compliant filter elements are expensive, and can represent a substantial portion of the sale price of a HEPA-compliant filter-fan unit. While such filter-fan units can condition the air by removing large particles, particulate matter small enough to pass through the filter element, including bacteria viruses and mold, for example, may not be removed.

Thus, new methods are needed to sanitize air that may contain microorganisms such as bacteria, viruses or mold.

BRIEF DESCRIPTION OF THE FIGURES

FIG. 12A-12B illustrate plan views of the germicidal lamp and an engaging receptacle in accordance with one embodiment of the present invention.

DETAILED DESCRIPTION

In an embodiment, the invention includes a housing having a germicidal lamp positioned in its interior. The housing can have vents around its exterior through which air can pass. The housing can contain a baffle system inside the vented housing such that air is directed through the interior of the device and is exposed to a sufficient amount of germicidal light during its passage through the device that the viability of microorganisms such as bacteria, mold or viruses is reduced. The device also can contain shielding to block the light from exiting the housing such that only conditioned air passes from the interior to the exterior.

In an embodiment the device can have operational controls located on a removable top portion. The controls can be positioned on the upper surface of the top portion or on the bottom of the lid such that they cannot be seen on the exterior of the device when the top portion is assembled on the base of the housing. Such controls can be utilized to control fan speed and light intensity in a known manner.

In an embodiment, the present invention includes an air transporting and/or conditioning system that includes a housing, an emitter electrode within the housing, a collector electrode within the housing located downstream from the emitter electrode, and a germicidal lamp configured to emit germicidal light. This system may further include a driver electrode that can be removable from the housing through a side portion of the housing. The driver electrode can be insulated with a dielectric material and/or a catalyst. A removable trailing electrode can also be configured within the housing and located downstream from the collector electrode. A first voltage source can be electrically coupled to the emitter electrode and the collector electrode, and a second voltage source can be electrically coupled to the trailing electrode. The second voltage source can be independently and selectively controllable with respect to the first voltage source.

Figure 1A:
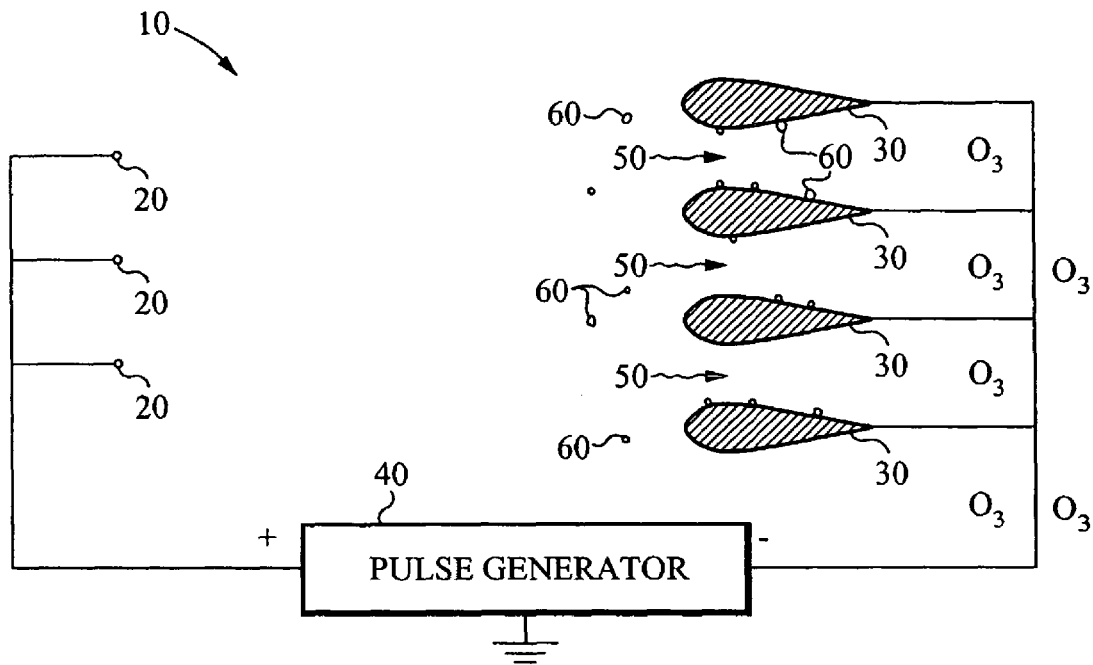
FIGS. 1A and 1B illustrate plan, cross-sectional views of a prior art electro-kinetic air transporter-conditioner system.
Figure 1B:
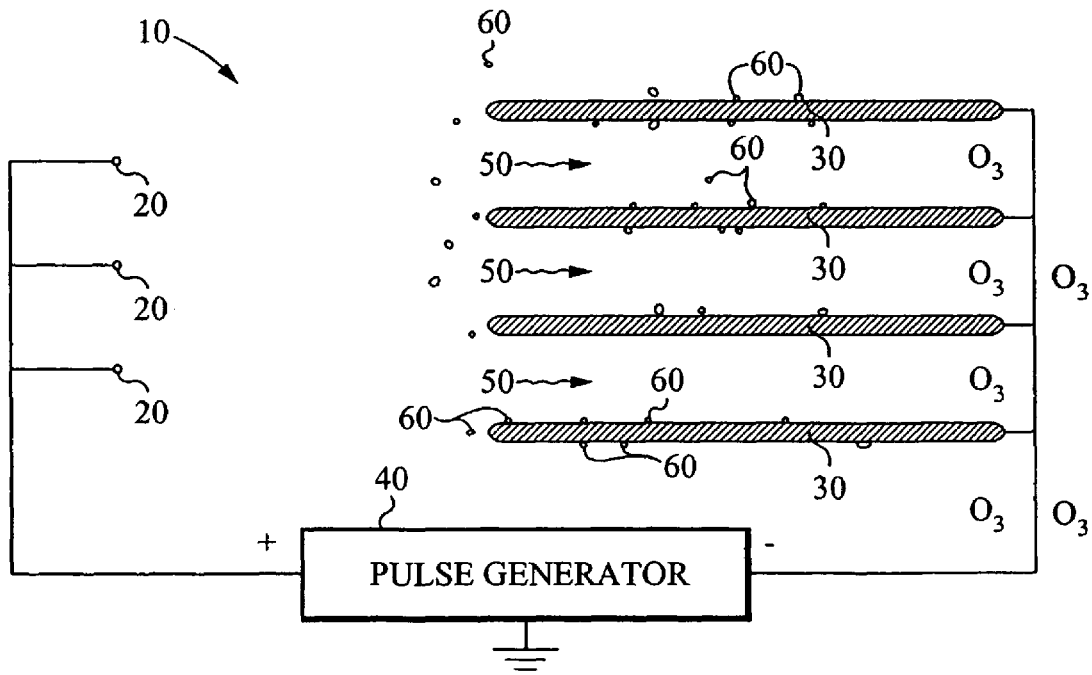
Figure 2:
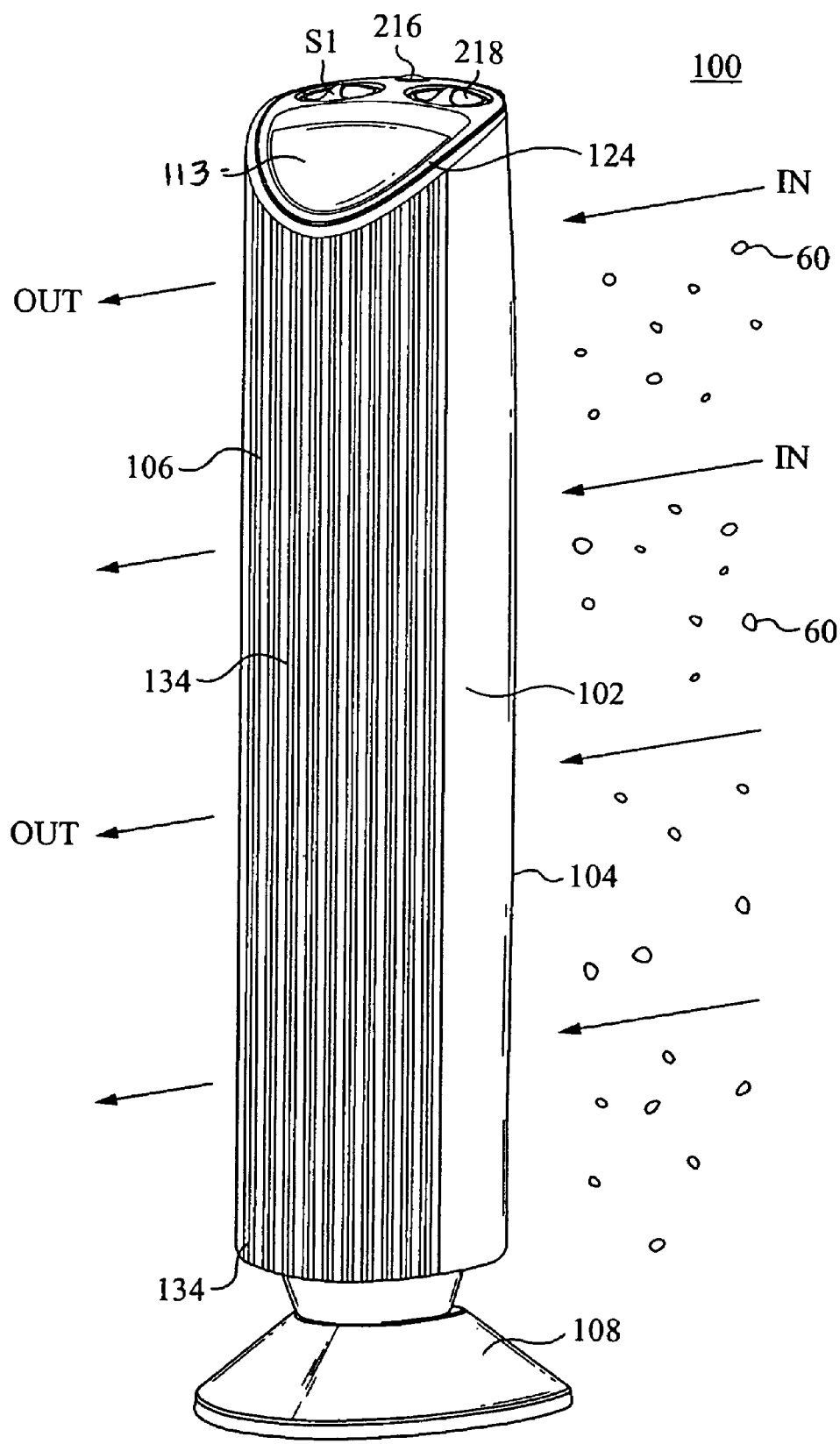
FIG. 2 illustrates a perspective view of the system in accordance with one embodiment of the present invention.

FIG. 2 depicts one embodiment of the air transporter-conditioner system 100 that can include a housing 102. The housing 102 can include a removable rear-located inlet or intake grill 104, a removable front-located outlet or exhaust grill 106, and a base pedestal 108. In another embodiment, a single grill can provide both an air intake and an air exhaust function, with an air inlet channel and an air exhaust channel that can be in communication with the grill and the air movement system within. In yet another embodiment, housing 102 can be constructed such that it has a single, unitary and cylindrical housing with no removable grills. The housing can have any suitable shape. For example, the housing 102 can be freestanding, vertically upstanding and/or elongated. The general shape of the housing 102 in the embodiment shown in FIG. 2 can be of an oval, rectangular, triangular, or any suitable cross-section. Alternatively, the housing 102 can include a differently shaped cross-section such as, but not limited to, a rectangular shape, a figure-eight shape, an egg shape, a tear-drop shape, a circular shape, or other suitable shape.

In one embodiment, an air movement system, which can include an ion generating unit 220 (FIG. 3) also referred to as an electrode assembly, can be located internal to the transporter housing 102. In one embodiment, the ion generating unit 220 (FIG. 3) can be self-contained in that, other than ambient air, nothing is required from beyond the housing 102 (except external operating potential) for operation of the present invention. In another embodiment, the air movement system can include a fan (not shown), which can be configured to supplement and/or replace the movement of air caused by the operation of the ion generating unit 220. In one embodiment, the system 100 can include a germicidal lamp 290 (FIG. 4) that is capable of reducing the amount of viable microorganisms exposed to the lamp 290 when they pass through the system 100. The germicidal lamp 290 (FIG. 4) will be capable of diminishing or destroying the viability of bacteria, mold, and viruses.

Figure 4:
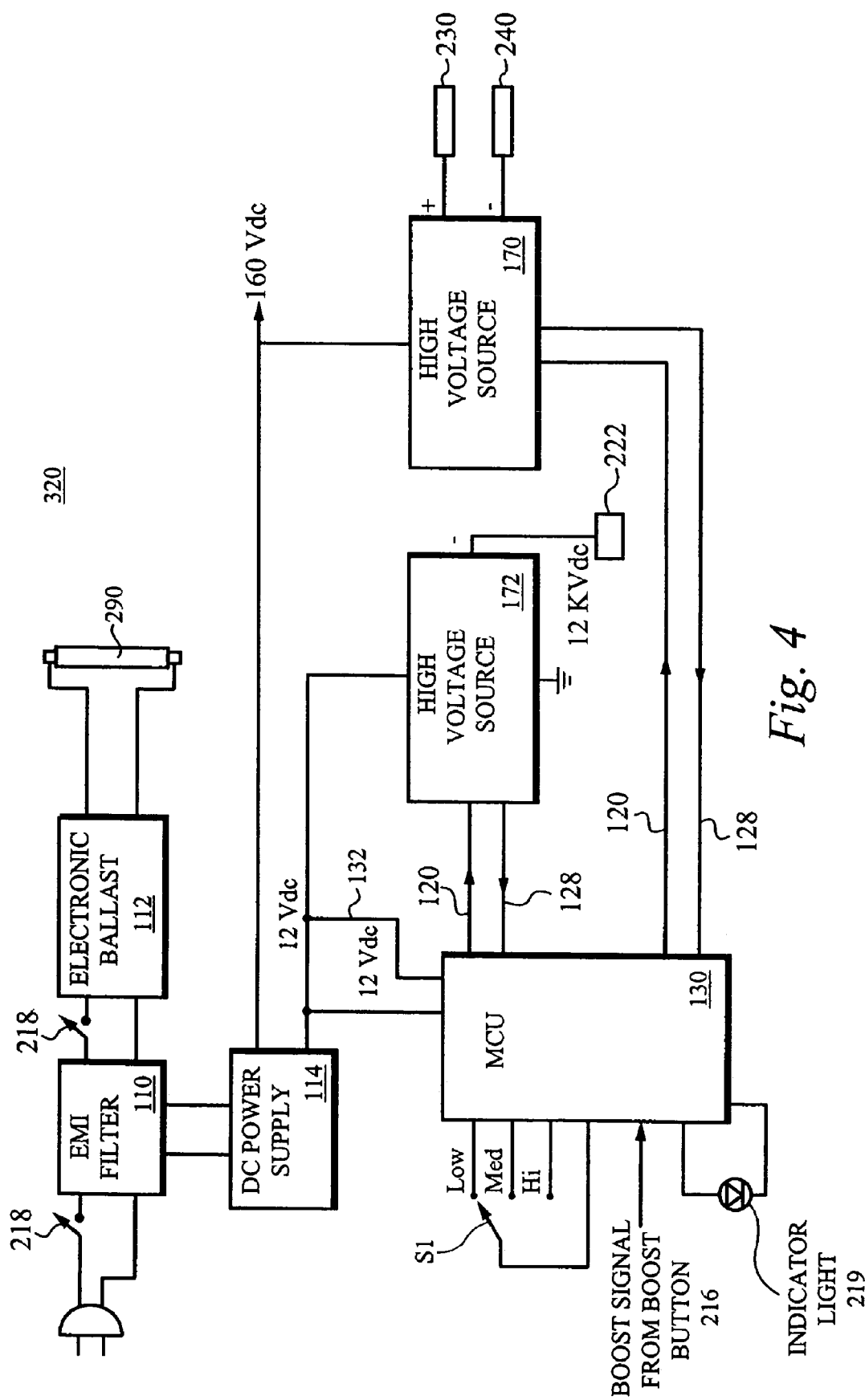
FIG. 4 illustrates a block diagram of one embodiment of the present invention.

In one embodiment, the ion generating unit 220 can be powered by an AC:DC power supply. The AC:DC power supply can be energizable or excitable using a switch S1, which can be conveniently located at the top 124 of the housing 102. The function dial 218 can enable a user to operate the germicidal lamp 290 (FIG. 4). In one embodiment, the user can select the dial 218 to "ON," "ON/GP," or "OFF." In the "ON" setting, the germicidal lamp 290 may not operate or emit germicidal light, although the electrode assembly 220 may be in operation. In the "ON/GP" setting, the germicidal lamp 290 can operate to remove or kill bacteria within the airflow while the electrode assembly 220 is in operation. In one embodiment, the electrode assembly 220 and the germicidal lamp 290 may not operate when the function dial or switch 218 is set to the "OFF" setting. Additionally, a boost button 216, which can boost the ion output of the ion generator 220, can be located at the top 124 of the housing 102. The boost operation will be discussed below. In one embodiment, one or more of the switch S1, function dial 218, and boost button 216 can be located on an outer surface of the top 124 of the housing 102. Alternatively, in another embodiment, one or more of the switch S1, function dial 218, and boost button 216 can be located on an inner surface of the top 124 of the housing and can be accessible by a user by removing the top 124 of the housing 102.

In one embodiment, both the intake and the exhaust grills 104, 106 can be covered by fins 134, also referred to as louvers. In one embodiment, each fin 134 can be a thin ridge spaced apart from an adjacent fin 134 such that each fin 134 can create minimal resistance as air flows through the housing 102. As shown in FIG. 2, the fins 134 can be vertical and can be directed along the elongated, vertical upstanding housing 102 of the system 100 in one embodiment. Alternatively, in another embodiment, the fins 134 can be perpendicular to the elongated housing 102 and can be configured horizontally. In one embodiment, the intake and exhaust fins 134 can be aligned to give the housing 102 a "see through" appearance while preventing an individual from viewing the germicidal light directly emitted from the germicidal lamp 290.

Figure 3:
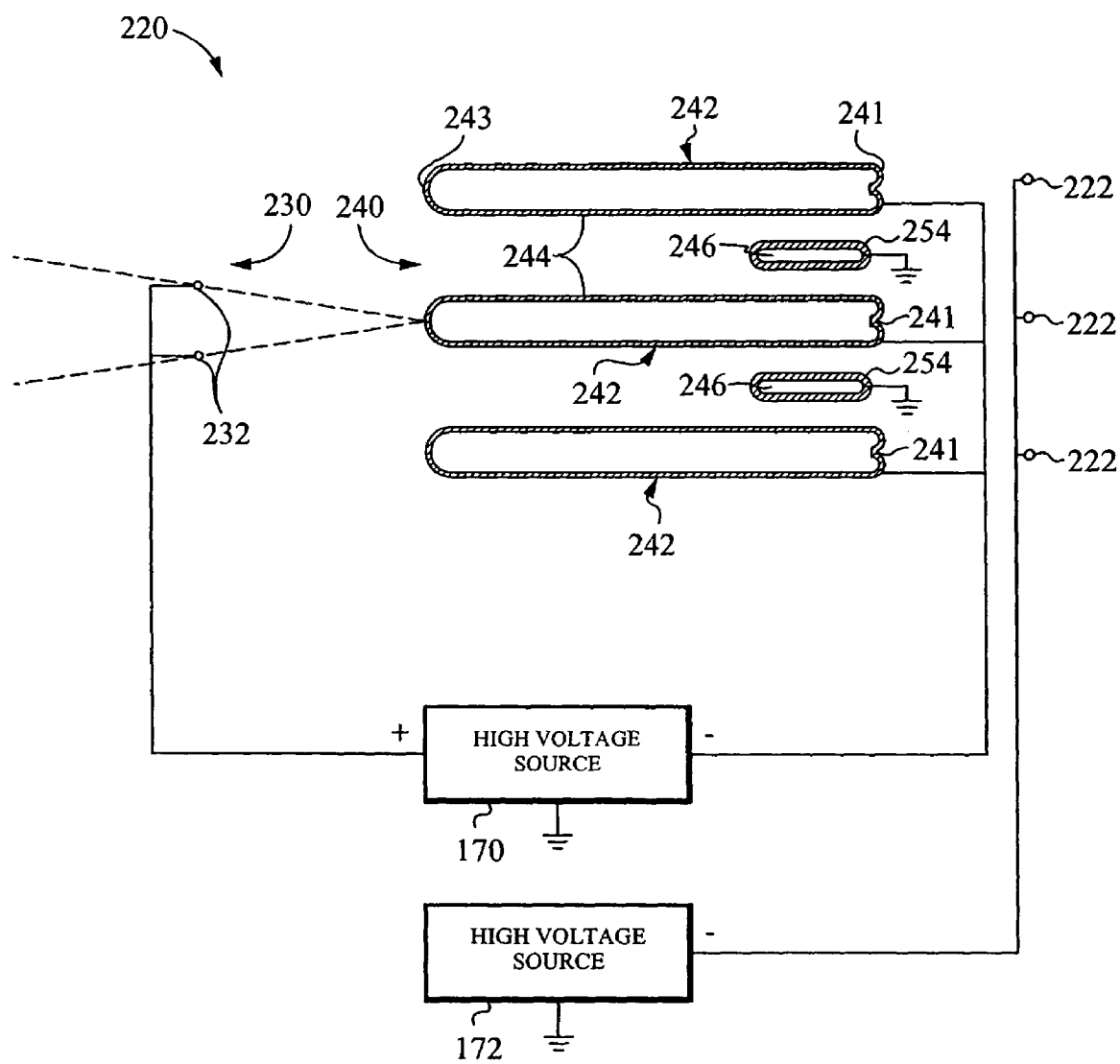
FIG. 3 illustrates a plan view of the electrode assembly in accordance with one embodiment of the present invention.

In an embodiment, there is no distinction between intake and exhaust grills 104 and 106, except their location relative to the collector electrodes 242 (FIG. 3). Alternatively, the intake and exhaust grills 104 and 106 can be configured differently and can be distinct from one another. The intake and exhaust grills 104, 106 can ensure that an adequate flow of ambient air can be drawn into or made available to the system 100 via the intake grill 104, and that an adequate flow of ionized air including appropriate amounts of ozone flows out from the system 100 via the exhaust grill 106. Thus, in one embodiment, the IN flow can enter via intake grill(s) 104, and the OUT flow can exit via exhaust grill(s) 106, as shown in FIG. 2.

In an embodiment, the system 100 can be energized by activating switch S1 such that a high voltage or high potential output by the ion generating unit 220 can produce ions within the system 100. The "IN" notation in FIG. 2 denotes the intake of ambient air with particulate matter 60 through the intake grill 104. The "OUT" notation in FIG. 2 denotes the outflow of cleaned air through the exhaust grill 106 substantially devoid of the particulate matter 60. It is to be understood that, although the flow of air in FIG. 2 is shown to move in a right to left direction, the air can, alternatively, flow in through the bottom of the housing 102 and out through the top 124 of the housing 102 and vice versa.

FIG. 3 illustrates a plan view of the electrode assembly in accordance with one embodiment of the present invention. The electrode assembly 220 can include a first electrode set 230 having emitter electrodes 232 and a second electrode set 240 having collector electrodes 242, which can be located downstream from the first electrode set 230. In the embodiment shown in FIG. 3, the electrode assembly 220 can also include a set of driver electrodes 246, which can be located interstitially between the collector electrodes 242. The electrode assembly 220 can additionally include a set of trailing electrodes 222 located downstream from the collector electrodes 242. In one embodiment, the number N1 of emitter electrodes 232 in the first set 230 can differ from the number N2 of collector electrodes 242 in the second set 240 by one. For example, the system 100 can include a greater number of collector electrodes 242 than emitter electrodes 232. However, if desired, additional emitter electrodes 232 can be located at the outer ends of the first set 230 such that N1>N2, e.g., five emitter electrodes 232 compared to four collector electrodes 242. Alternatively, in another embodiment, single electrodes or single conductive surfaces can be used instead of multiple electrodes. It is to be understood that other numbers and arrangements of emitter electrodes 232, collector electrodes 242, trailing electrodes 222 and driver electrodes 246 can be configured in the electrode assembly 220 in other embodiments.

In one embodiment, the material(s) of the electrodes 232 and 242 can conduct electricity and can be resistant to corrosive effects from the application of high voltage, but yet can be strong and durable enough to be cleaned periodically. In one embodiment, the emitter electrodes 232 can be fabricated from tungsten. Tungsten is sufficiently robust to withstand cleaning, has a high melting point to retard breakdown due to ionization, and has a rough exterior surface to promote efficient ionization. In one embodiment, the collector electrodes 242 can have a highly polished exterior surface to minimize unwanted point-to-point radiation. As such, the collector electrodes 242 can be fabricated from stainless steel, brass, and/or other suitable materials. The polished surface of the collector electrodes 242 can also promote ease of electrode cleaning. Due to the materials and construction of the emitter and collector electrodes 232 and 242, the electrodes 232, 242 can be light weight, easy to fabricate, and can lend themselves to mass production. Further, the emitter and collector electrodes 232 and 242 described herein can promote more efficient generation of ionized air and appropriate amounts of ozone.

As shown in FIG. 3, one embodiment of the present invention can include a first high voltage source (HVS) 170 and a second high power voltage source 172. The positive output terminal of the first HVS 170 can be coupled to the emitter electrodes 232, and the negative output terminal of the first HVS 170 can be coupled to the collector electrodes 242. This coupling polarity has been found to work well and minimizes unwanted audible electrode vibration or hum. It is to be understood that in some embodiments, one port such as, for example, the negative port of the high voltage power supply can be ambient air. Thus, it is not necessary for the collector electrodes 242 in the second electrode set 240 to be connected to the first HVS 170 using a wire. Nonetheless, there can be an "effective connection" between the collector electrodes 242 and one output port of the first HVS 170, in this instance via ambient air. Alternatively, in one embodiment, the negative output terminal of the first HVS 170 can be connected to the first electrode set 230, and the positive output terminal can be connected to the second electrode set 240.

In one embodiment, when voltage or pulses from the first HVS 170 are generated across the first and second electrode sets 230 and 240, a plasma-like field can be created that surrounds the emitter electrodes 232 in the first electrode set 230. This electric field can ionize the ambient air between the first and the second electrode sets 230, 240 and can establish an "OUT" airflow that moves toward the second electrode set 240, herein referred to as the ionization region.

In one embodiment, ozone and ions can be generated simultaneously by the emitter electrodes 232 as a function of the voltage potential from the first HVS 170. Ozone generation can be increased or decreased by increasing or decreasing the voltage potential at the first electrode set 230. Coupling an opposite polarity voltage potential to the collector electrodes 242 can accelerate the motion of ions from the first electrode set 230 to the second electrode set 240, thereby producing the airflow in the ionization region. Molecules, as well as particulates in the air, can become ionized with the charge emitted by the emitter electrodes 232 as the airflow passes by the electrodes 232. As the ions and ionized particulates move toward the second electrode set 240, the ions and ionized particles can push or move air molecules toward the second electrode set 240. The relative velocity of this motion can be increased by, for example, increasing the voltage potential at the second electrode set 240 relative to the potential at the first electrode set 230. Therefore, the collector electrodes 242 can collect the ionized particulates in the air, thereby allowing the system 100 to output cleaner, fresher air.

As shown in the embodiment in FIG. 3, at least one output trailing electrode 222 can be electrically coupled to the second HVS 172. The trailing electrode 222 can generate a substantial amount of negative ions when the electrode 222 is coupled to a relatively negative high potential. In one embodiment, the trailing electrode(s) 222 can be a wire located downstream from the collector electrodes 242. In one embodiment, the collector electrode 222 can have a pointed shape in its side profile (e.g., a triangle) as described in U.S. patent application Ser. No. 10/074,347, which is incorporated by reference in its entirety.

In one embodiment, the negative ions produced by the trailing electrode 222 can neutralize excess positive ions present in the output airflow such that the OUT flow can have a net negative charge. The trailing electrodes 222 can be made of stainless steel, copper, or other conductor material. It has been found that the inclusion of one trailing electrode 222 can be sufficient to provide a sufficient number of output negative ions. However, multiple trailing electrodes 222 can be utilized in other embodiments. Details regarding the trailing electrode 222 are described in the 60/590,735 application, which is incorporated by reference in its entirety.

In one embodiment, the use of the driver electrodes 246 can increase the particle collection efficiency of the electrode assembly 220 and can reduce the percentage of particles that are not collected by the collector electrode 242. This can be due to the driver electrode 246 pushing particles in the airflow toward the inside surface 244 of the adjacent collector electrode(s) 242, which is referred to herein as the collecting region. The driver electrode 246 can be insulated, which can further increase particle collection efficiency.

As stated above, the system of the present invention in some circumstances may produce ozone ($O_3$). In one embodiment, ozone production can be reduced by coating the internal surfaces of the housing with an ozone reducing catalyst. Exemplary ozone reducing catalysts can include manganese dioxide and activated carbon. Commercially available ozone reducing catalysts such as, for example, PremAir™ manufactured by Englehard Corporation of Iselin, N. J., can alternatively be used. Some ozone reducing catalysts can be electrically conductive, while others may not be electrically conductive (e.g., manganese dioxide). In one embodiment, the ozone reducing catalysts can have a dielectric strength of at least 1000 V/mil (one-hundredth of an inch).

In one embodiment, the driver electrode 246 can include an electrically conductive electrode that can be coated with an insulating dielectric material 254. In embodiments where the driver electrode 246 is not insulated, the driver electrode 246 can include an electrically conductive electrode only. In one embodiment, the insulating dielectric material 254 can be a heat shrink material (e.g., a flexible polyolefin material). In another embodiment, the insulating dielectric material 254 can be an insulating varnish, lacquer or resin. Other possible insulating dielectric materials 254 that can be used to insulate the driver electrode 246 include, but are not limited to, ceramic, porcelain enamel, fiberglass, and the like.

In one embodiment, the driver electrodes 246 can be electrically connected to ground, as shown in FIG. 3. Although the grounded driver electrodes 246 may not receive a charge from either the first or second HVS 170, 172, the driver electrodes 246 can still deflect positively charged particles toward the collector electrodes 242. In another embodiment, the driver electrodes 246 can be positively charged. In yet another embodiment, the driver electrodes 246 can be electrically coupled to the negative terminal of either the first or second HVS 170, 172 such that the driver electrodes 246 can be charged at a voltage that can be less than the negatively charged collector electrodes 242. Details regarding the insulated driver electrodes 246 are described in the 60/590,960 application, which is incorporated by reference in its entirety.

FIG. 4 illustrates an electrical circuit diagram for the system 100 according to one embodiment of the present invention. The system 100 can have an electrical power cord that can plug into a common electrical wall socket to provide a nominal 110 VAC. An electromagnetic interference (EMI) filter 110 can be placed across the incoming nominal 110 VAC line to reduce and/or eliminate high frequencies generated by the various circuits within the system 100 such as, for example, the electronic ballast 112. In one embodiment, the electronic ballast 112 can be electrically connected to a germicidal lamp 290 (e.g., an ultraviolet lamp) to regulate or control the flow of current through the germicidal lamp 290. In one embodiment, a switch 218 can be used to turn the germicidal lamp 290 on or off. The EMI filter 110 is well known in the art and, thus, does not require a further description. In another embodiment, the germicidal lamp 290 can be eliminated entirely from the system 100. Thus, in such an embodiment, the electronic ballast 112, the germicidal lamp 290, and the switch 218 used to operate the germicidal lamp 290 can be eliminated from the circuit diagram shown in FIG. 4.

In one embodiment, the EMI filter 110 can be coupled to a DC power supply 114. The DC power supply 114 can be coupled to the first HVS 170 and to the second HVS 172. The first and second HVSs 170, 172 can also be referred to as pulse generators. In one embodiment, the DC power supply 114 can also be coupled to a micro-controller unit (MCU) 130. The MCU 130 can be, for example, a Motorola 68HC908 series micro-controller, which is available from Motorola. Alternatively, any other type of MCU can be contemplated. In one embodiment, the MCU 130 can receive a signal from the switch S1 and a boost signal from the boost button 216. In one embodiment, the MCU 130 can also include an indicator light 219, which can specify when the electrode assembly is ready to be cleaned.

In one embodiment, the DC power supply 114 can be designed to receive the incoming nominal 110 VAC and to output a first DC voltage (e.g., approximately 160 VDC) to the first HVS 170. The DC power supply 114 voltage (e.g., approximately 160 VDC) can also be stepped down to a second DC voltage (e.g., approximately 12 VDC) for powering the micro-controller unit (MCU) 130, the second HVS 172, and other internal logic of the system 100. In other embodiments, the voltage can be stepped down through a resistor network, transformer or other suitable component.

As shown in the embodiment of FIG. 4, the first HVS 170 can be coupled to the first electrode set 230 and the second electrode set 240 to provide a potential difference between the first and second electrode sets 230, 240. In one embodiment, the first HVS 170 can be electrically coupled to the driver electrode 246, as described above. Additionally, in one embodiment, the first HVS 170 can be coupled to the MCU 130 such that the MCU 130 can receive arc sensing signals 128 from the first HVS 170 and provide low voltage pulses 120 to the first HVS 170. The second HVS 172, which can provide a voltage to the trailing electrodes 222, is also shown in the embodiment of FIG. 4. In one embodiment, the second HVS 172 can be coupled to the MCU 130 such that the MCU 130 can receive arc sensing signals 128 from the second HVS 172 and provide low voltage pulses 120 to the second HVS 172.

In one embodiment, the MCU 130 can monitor the stepped down voltage (e.g., approximately 12 VDC), which is referred to as the AC voltage sense signal 132 in FIG. 4, to determine if the AC line voltage is above or below the nominal 110 VAC and to sense changes in the AC line voltage. For example, if a nominal 110 VAC increases by 10% to approximately 121 VAC, then the stepped down DC voltage can also increase by 10%. The MCU 130 can sense this increase and appropriately reduce the pulse width, duty cycle and/or frequency of the low voltage pulses to maintain the output power (provided to the first HVS 170) to be the same as when the line voltage is at 110 VAC. Conversely, when the line voltage drops, the MCU 130 can sense this decrease and appropriately increase the pulse width, duty cycle and/or frequency of the low voltage pulses to maintain a constant output power. Such voltage adjustment features of the present invention can enable the same system 100 to be used in different countries having different nominal voltages from the United States. For example, the nominal AC voltage in Japan is 100 VAC.

Figure 5:
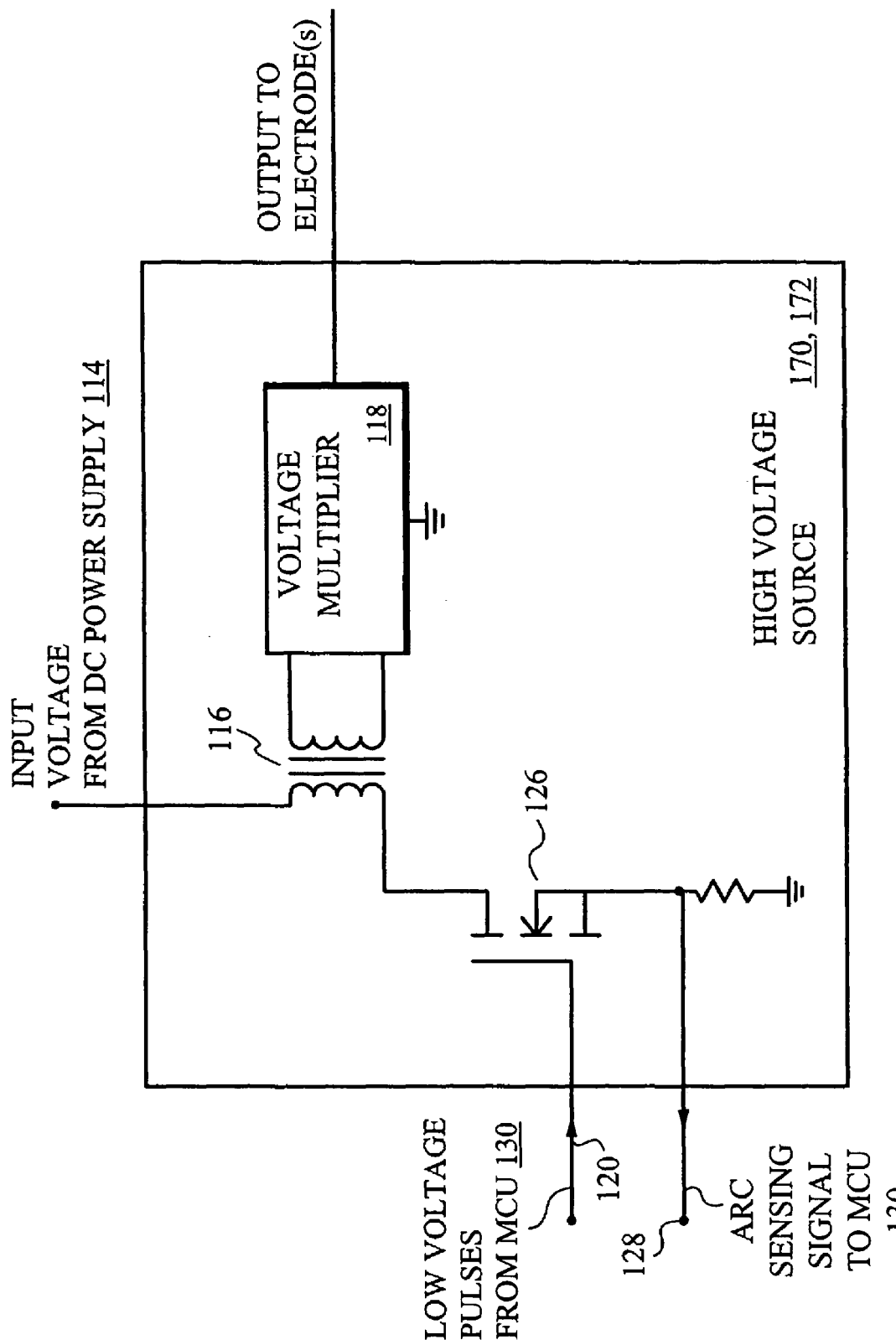
FIG. 5 illustrates a block diagram of one embodiment of the present invention.

FIG. 5 illustrates a block diagram of the high voltage power supply in accordance with one embodiment. For purposes of the present description, the first and second HVSs 170, 172 can include the same or similar components as that shown in FIG. 5. However, it is to be understood by one skilled in the art that the first and second HVSs 170, 172 can, alternatively, include different components from each other as well as from those shown in FIG. 5. In one embodiment, the various circuits and components that make up the first and second HVSs 170, 172 can, for example, be fabricated on a printed circuit board mounted within the housing 102. The MCU 130 can be located on the same circuit board or on a different circuit board.

In the embodiment shown in FIG. 5, the first and second HVSs 170, 172 can include an electronic switch 126, a step-up transformer 116 and a voltage multiplier 118. In one embodiment, the primary side of the step-up transformer 116 can receive the DC voltage from the DC power supply 114. For the first HVS 170, the DC voltage received from the DC power supply 114 can be approximately 160 Vdc. For the second HVS 172, the DC voltage received from the DC power supply 114 can be approximately 12 Vdc. In one embodiment, an electronic switch 126 can receive low voltage pulses 120 (such as, for example, 20-25 KHz frequency) from the MCU 130. As shown, such a switch can be an insulated gate bipolar transistor (IGBT) 126. In one embodiment, the IGBT 126, or other suitable switch, can couple the low voltage pulses 120 from the MCU 130 to the input winding of the step-up transformer 116. In one embodiment, the secondary winding of the step-up transformer 116 can be coupled to the voltage multiplier 118, which can output the high voltage pulses to the electrode(s). In one embodiment, the electrode (s) for the first HVS 170 can include the first and second electrode sets 230 and 240. In one embodiment, the electrode (s) for the second HVS 17 can be the trailing electrodes 222. In general, the IGBT 126 can operate as an electronic on/off switch. Such a transistor is well known in the art and is, thus, not further described.

In one embodiment, the first and second HVSs 170, 172 can receive the low input DC voltage from the DC power supply 114 and low voltage pulses from the MCU 130 when driven and can generate high voltage pulses of, for example, at least approximately 5 KV peak-to-peak with a repetition rate of approximately 20 to 25KHz. In one embodiment, the voltage multiplier 118 in the first HVS 170 can output between approximately 5 to approximately 9 KV to the first electrode set 230 and between approximately −6 to approximately −18 KV to the second electrode set 240. In one embodiment, the emitter electrodes 232 can receive approximately 5 to approximately 6 KV, whereas the collector electrodes 242 can receive approximately −9 to approximately −10 KV. In one embodiment, the voltage multiplier 118 in the second HVS 172 can output approximately −12 KV to the trailing electrodes 222. In one embodiment, the driver electrodes 246 can be connected to ground. It is to be understood that the voltage multiplier 118 can produce greater or smaller voltages. In one embodiment, the high voltage pulses can have a duty cycle of approximately 10% to approximately 15%, but may have other duty cycles, including a 100% duty cycle, if desired.

In one embodiment, the MCU 130 can be coupled to a control dial S1, as discussed above, which can be set to a LOW, MEDIUM or HIGH airflow setting as shown in FIG. 4. In one embodiment, the MCU 130 can control the amplitude, pulse width, duty cycle and/or frequency of the low voltage pulse signal to control the airflow output of the system 100 based on the setting of the control dial S1. In one embodiment, to increase the airflow output, the MCU 130 can be set to increase the amplitude, pulse width, frequency and/or duty cycle. Conversely, in one embodiment, to decrease the airflow output rate, the MCU 130 can reduce the amplitude, pulse width, frequency and/or duty cycle. In one embodiment, the low voltage pulses 120 can have a fixed pulse width, frequency and duty cycle for the LOW setting, can have another fixed pulse width, frequency and duty cycle for the MEDIUM setting, and can have a further fixed pulse width, frequency and duty cycle for the HIGH setting.

In one embodiment, the low voltage pulse 120 can modulate between a predetermined duration of a "high" airflow signal and a "low" airflow signal. In one embodiment, the low voltage signal can modulate between a predetermined amount of time in which the airflow can be at the greater "high" flow rate, followed by another predetermined amount of time in which the airflow can be at the lesser "low" flow rate. In one embodiment, this can be executed by adjusting the voltages provided by the first HVS 170 to the first and second electrode set 230, 240 for the greater flow rate period and the lesser flow rate period. This can produce an acceptable airflow output while limiting the ozone production to acceptable levels, regardless of whether the control dial S1 is set to HIGH, MEDIUM or LOW. For example, in one embodiment, the "high" airflow signal can have a pulse width of approximately 5 microseconds and a period of approximately 40 microseconds (i.e., a 12.5% duty cycle), and the "low" airflow signal can have a pulse width of approximately 4 microseconds and a period of approximately 40 microseconds (i.e., a 10% duty cycle).

In one embodiment, the voltage difference between the first electrode set 230 and the second electrode set 240 can be proportional to the actual airflow output rate of the system 100. Thus, a greater voltage differential can be created between the first and second electrode sets 230, 240 by the "high" airflow signal, whereas a lesser voltage differential can be created between the first and second electrode sets 230, 240 by the "low" airflow signal. In one embodiment, the airflow signal can cause the voltage multiplier 118 to provide between approximately 5 and approximately 9 KV to the first electrode set 230 and between approximately −9 and approximately −10 KV to the second electrode set 240. For example, the "high" airflow signal can cause the voltage multiplier 118 to provide approximately 5.9 KV to the first electrode set 230 and approximately −9.8 KV to the second electrode set 240. In the example, the "low" airflow signal can cause the voltage multiplier 118 to provide approximately 5.3 KV to the first electrode set 230 and approximately −9.5 KV to the second electrode set 240. It is to be understood that the MCU 130 and the first HVS 170 can produce voltage potential differentials between the first and second electrode sets 230 and 240 other than the values provided above and, thus, the present invention is in no way limited by the values specified.

In one embodiment, when the control dial S1 is set to HIGH, the electrical signal output from the MCU 130 can drive the first HVS 170 and the airflow such that the electrical signal output can modulate between the "high" and "low" airflow signals stated above (e.g., approximately 2 seconds "high" and approximately 10 seconds "low"). In one embodiment, when the control dial S1 is set to MEDIUM, the electrical signal output from the MCU 130 can cyclically drive the first HVS 170 (i.e., airflow is "On") for a predetermined amount of time (e.g., approximately 20 seconds), and then drop to a zero or a lower voltage for a further predetermined amount of time (e.g., approximately 20 additional seconds). It is to be understood that the cyclical drive when the airflow is "On" can be modulated between the "high" and "low" airflow signals (e.g., approximately 2 seconds "high" and approximately 10 seconds "low"), as stated above. In one embodiment, when the control dial S1 is set to LOW, the signal from the MCU 130 can cyclically drive the first HVS 170 (i.e., airflow is "On") for a predetermined amount of time (e.g., approximately 20 seconds), and then drop to a zero or a lower voltage for a longer time period (e.g., approximately 80 seconds). Again, it is to be understood that the cyclical drive when the airflow is "On" can be modulated between the "high" and "low" airflow signals (e.g., approximately 2 seconds "high" and approximately 10 seconds "low"), as stated above. It is to be understood that the HIGH, MEDIUM, and LOW settings can drive the first HVS 170 for longer or shorter periods of time. Also, it is to be understood that the cyclic drive between "high" and "low" airflow signals can have durations and voltages other than those described herein.

In one embodiment, cyclically driving airflow through the system 100 for a period of time, followed by little or no airflow for another period of time (i.e., MEDIUM and LOW settings) can allow the overall airflow rate through the system 100 to be slower than when the dial S1 is set to HIGH. Additionally, in one embodiment, cyclical driving can reduce the amount of ozone emitted by the system since little or no ions are produced during the period in which little or no airflow is being output by the system. Further, in one embodiment, the duration in which little or no airflow is driven through the system 100 can provide the air already inside the system a longer dwell time, which can increase particle collection efficiency. In one embodiment, the long dwell time can allow air to be exposed to a germicidal lamp, if present.

Regarding the second HVS 172, approximately 12 volts DC can be applied to the second HVS 172 from the DC power supply 114. In one embodiment, the second HVS 172 can provide a negative charge (e.g., approximately −12 KV) to one or more trailing electrodes 222. However, in other embodiments, the second HVS 172 can provide a voltage in the range of, and including approximately −10 KV to approximately −60 KV. In yet other embodiments, other voltages produced by the second HVS 172 can be used.

In one embodiment, the second HVS 172 can be controllable independently from the first HVS 170 by, for example, the boost button 216, which can allow the user to increase or decrease the amount of negative ions output by the trailing electrodes 222 without correspondingly increasing or decreasing the voltage provided to the first and second electrode sets 230, 240. The second HVS 172, thus, can provide freedom to operate the trailing electrodes 222 independently of the remainder of the electrode assembly 220 to reduce static electricity, eliminate odors and the like. Additionally, the second HVS 172 can allow the trailing electrodes 222 to operate at a different duty cycle, amplitude, pulse width, and/or frequency than the first and second electrode sets 230 and 240. In one embodiment, the user can vary the voltage supplied by the second HVS 172 to the trailing electrodes 222 at any time by depressing the boost button 216. In one embodiment, the user can turn on or turn off the second HVS 172 and, thus, the trailing electrodes 222 without affecting operation of the electrode assembly 220 and/or the germicidal lamp 290. It is to be understood that, in one embodiment, the second HVS 172 can also be used to control electrical components other than the trailing electrodes 222 (e.g., driver electrodes and the germicidal lamp).

As mentioned above, the system 100 can include a boost button 216. In one embodiment, the trailing electrodes 222 and the first and second electrode sets 230, 240 can be controlled by the boost signal from the boost button 216 input into the MCU 130. In one embodiment mentioned above, the boost button 216 can cycle through a set of operating settings upon the boost button 216 being depressed. In the example embodiment discussed below, the system 100 can include three operating settings. However, any number of operating settings is within the scope of the present invention.

The following discussion explains the methods of operation of the boost button 216, which can be variations of the methods discussed above. In one embodiment, the system 100 can operate in a first boost setting when the boost button 216 is pressed once. In the first boost setting, the MCU 130 can drive the first HVS 170 as if the control dial S1 was set to the HIGH setting for a predetermined amount of time (e.g., approximately 6 minutes), even if the control dial S1 is set to LOW or MEDIUM (in effect overriding the setting specified by the dial S1). The predetermined time period can be longer or shorter than 6 minutes. For example, the predetermined period can also be approximately 20 minutes if a higher cleaning setting for a longer period of time is desired. This can cause the system 100 to run at a maximum airflow rate for the predetermined boost time period. In one embodiment, the low voltage signal can modulate between the "high" airflow signal and the "low" airflow signal for predetermined amounts of time and voltages, as stated above, when operating in the first boost setting. In another embodiment, the low voltage signal does not modulate between the "high" and "low" airflow signals.

In one embodiment, the MCU 130 can also operate the second HVS 172 to operate the trailing electrode 222 and generate ions, e.g., negative ions, into the airflow in the first boost setting. In one embodiment, the trailing electrode 222 can emit ions for approximately one second and then terminate for approximately five seconds for the entire predetermined boost time period. The increased amounts of ozone from the boost level can further reduce odors in the entering airflow and can increase the particle capture rate of the system 100. In one embodiment, the system 100 can return to the airflow rate previously selected by the control dial S1 at the end of the predetermined boost period. It is to be understood that the on/off cycle at which the trailing electrodes 222 operates may not be limited to the cycles and periods described above.

In the example, once the boost button 216 is pressed again, the system 100 can operate in the second setting, which can be an increased ion generation or "feel good" mode. In the second setting, the MCU 130 can drive the first HVS 170 as if the control dial S1 was set to the LOW setting, even if the control dial S1 is set to HIGH or MEDIUM (in effect overriding the setting specified by the dial S1). Thus, the airflow may not be continuous, but "On" and then can be at a lesser or zero airflow for a predetermined amount of time (e.g., approximately 6 minutes). Additionally, in one embodiment, the MCU 130 can operate the second HVS 172 to operate the trailing electrode 222 and generate negative ions, for example, into the airflow. In one embodiment, the trailing electrode 222 can emit ions for approximately one second and then terminate for approximately five seconds for the predetermined amount of time. It is to be understood that the on/off cycle at which the trailing electrodes 222 operate may not be limited to the cycles and periods described above.

In the example, upon the boost button 216 being pressed again, the MCU 130 can operate the system 100 in a third operating setting, which can be a normal operating mode. In the third setting, the MCU 130 can drive the first HVS 170 depending on which setting the control dial S1 is set to (e.g., HIGH, MEDIUM or LOW). Additionally, the MCU 130 can operate the second HVS 172 to operate the trailing electrode 222 and generate negative ions, for example, into the airflow at a predetermined interval. In one embodiment, the trailing electrode 222 can emit ions for approximately one second and then can terminate emission for approximately nine seconds. In another embodiment, the trailing electrode 222 may not operate at all in this mode. The system 100 can continue to operate in the third setting by default until the boost button 216 is pressed. It should be noted that the on/off cycle at which the trailing electrodes 222 operate may not be limited to the cycles and periods described above.

In one embodiment, the present system 100 can operate in an automatic boost mode upon the system 100 being initially plugged into the wall and/or initially being turned on after being off for a predetermined amount of time. In particular, upon the system 100 being turned on, the MCU 130 can automatically drive the first HVS 170 as if the control dial S1 was set to the HIGH setting for a predetermined amount of time, as discussed above, even if the control dial S1 is set to LOW or MEDIUM, and can, thereby cause the system 100 to run at a maximum airflow rate for the amount of time. In addition, the MCU 130 can automatically operate the second HVS 172 to operate the trailing electrode 222 at a maximum ion emitting rate and generate negative ions, for example, into the airflow for the same amount of time. This configuration can allow the system 100 to clean stale, pungent, and/or polluted air in a room in which the system 100 has not been continuously operating in. This feature can improve the air quality at a faster rate while emitting negative "feel good" ions that can quickly eliminate any odor in the room. In one embodiment, the system 100 can automatically adjust the airflow rate and ion emitting rate to the third setting (i.e., normal operating mode) once the system 100 has been operating in the first setting boost mode. For example, in this initial plug-in or initial turn-on mode, the system can operate in the high setting for approximately twenty minutes to enhance the removal of particulates and to clean the air more rapidly as well as deodorize the room.

In one embodiment, the system 100 can include an indicator light, which informs the user what mode the system 100 is operating in when the boost button 216 is depressed. In one embodiment, the indicator light can be the same as the cleaning indicator light 219 discussed above. In another embodiment, the indicator light can be a separate light from the indicator light 219. For example, in one embodiment, the indicator light 219 can emit a blue light when the system 100 operates in the first setting. Additionally, in one embodiment, the indicator light 219 can emit a green light when the system 100 operates in the second setting. In these embodiments, the indicator light may not emit a light when the system 100 is operating in the third setting.

In one embodiment, the MCU 130 can provide various timing and maintenance features. For example, the MCU 130 can provide a cleaning reminder feature (e.g., an approximately two-week timing feature) that can provide a reminder to clean the system 100 (e.g., by causing indicator light 219 to turn amber and/or by triggering an audible alarm that can produce a buzzing or beeping noise). In one embodiment, the MCU 130 can also provide arc sensing, suppression and indicator features, as well as the ability to shut down the first HVS 170 in the case of continued arcing. Details regarding arc sensing, suppression and indicator features are described in U.S. patent application Ser. No. 10/625,401 which is incorporated by reference in its entirety.

In one embodiment, the MCU 130 can include a lamp timing feature which can notify the user that the germicidal lamp 290 is in need of replacement. In one embodiment, upon the timing feature counting a predetermined duration of suitable length (e.g., approximately 8000 operating hours), the MCU 130 can notify the user that the germicidal lamp 290 should be replaced. In one embodiment, the timing feature of the MCU 130 can toll the counting while the unit is off or unplugged. In one embodiment, the MCU 130 can notify the user using the indicator light 219 discussed above such that the indicator light can turn a different color and/or can begin flashing. In another embodiment, the system 100 can include a separate indicator. The lamp timing feature of the MCU 130 can be set by the manufacturer to the normal operating life of the germicidal lamp 290.

In one embodiment, the timing feature of the MCU 130 can be reset by the user. The timing feature can be reset by performing a combination of steps. This can prevent the user from inadvertently resetting the timer. For example, the timing feature can be reset by pressing the boost button 216 and turning the S1 switch to HIGH, either simultaneously or in quick succession, while the unit is off. The "high" airflow signal and the boost button signal can enter the MCU 130 to reset the timer circuit. In another embodiment, the timer feature can be reset by a mechanical switch in the receptacle 300 (FIG. 7), such that removing and/or inserting the germicidal lamp 290 into the receptacle 300 can reset the timer circuit.

Figure 6:
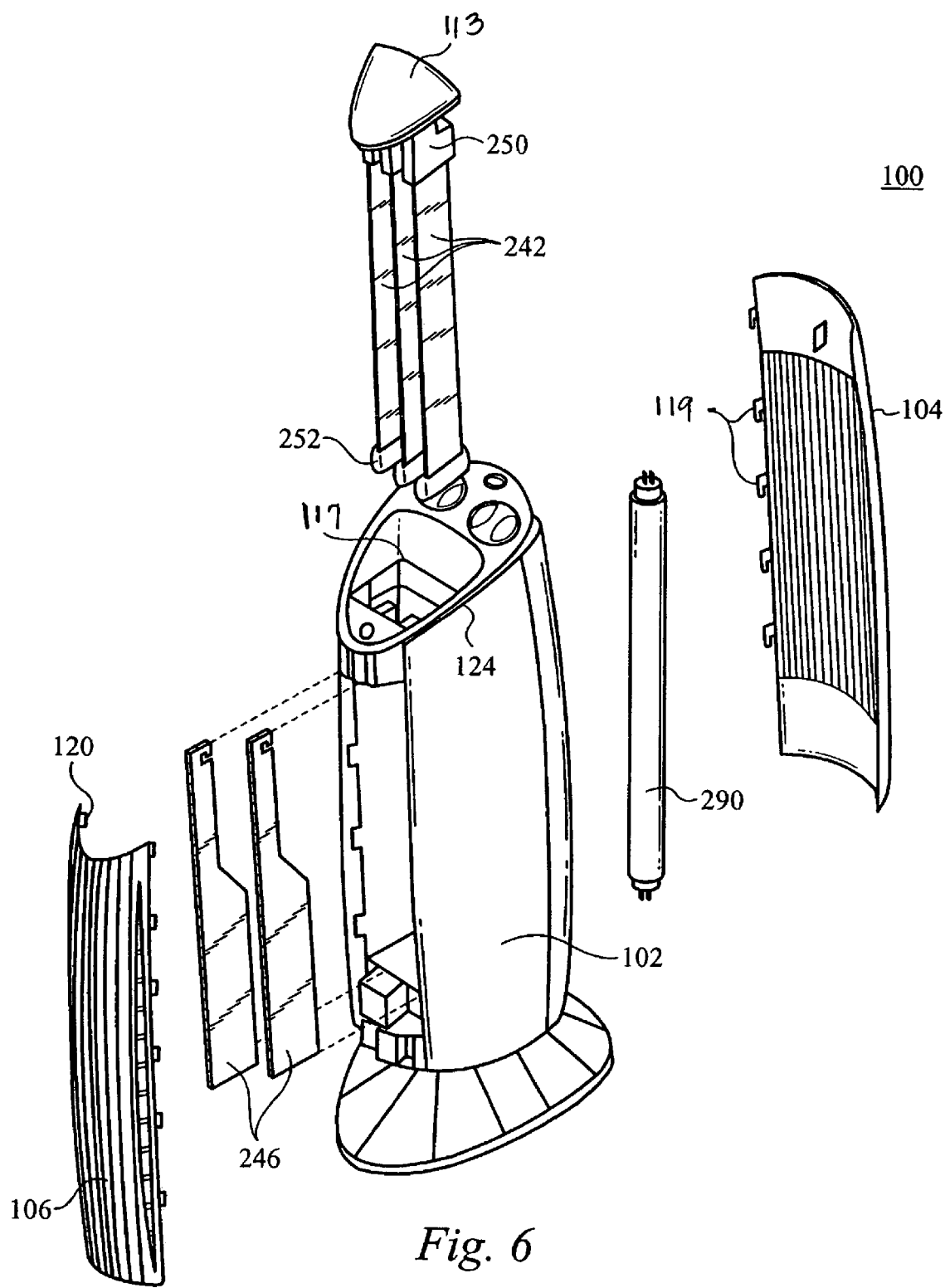
FIG. 6 illustrates an exploded view of the system shown in FIG. 2 in accordance with one embodiment of the present invention.
Figure 13:
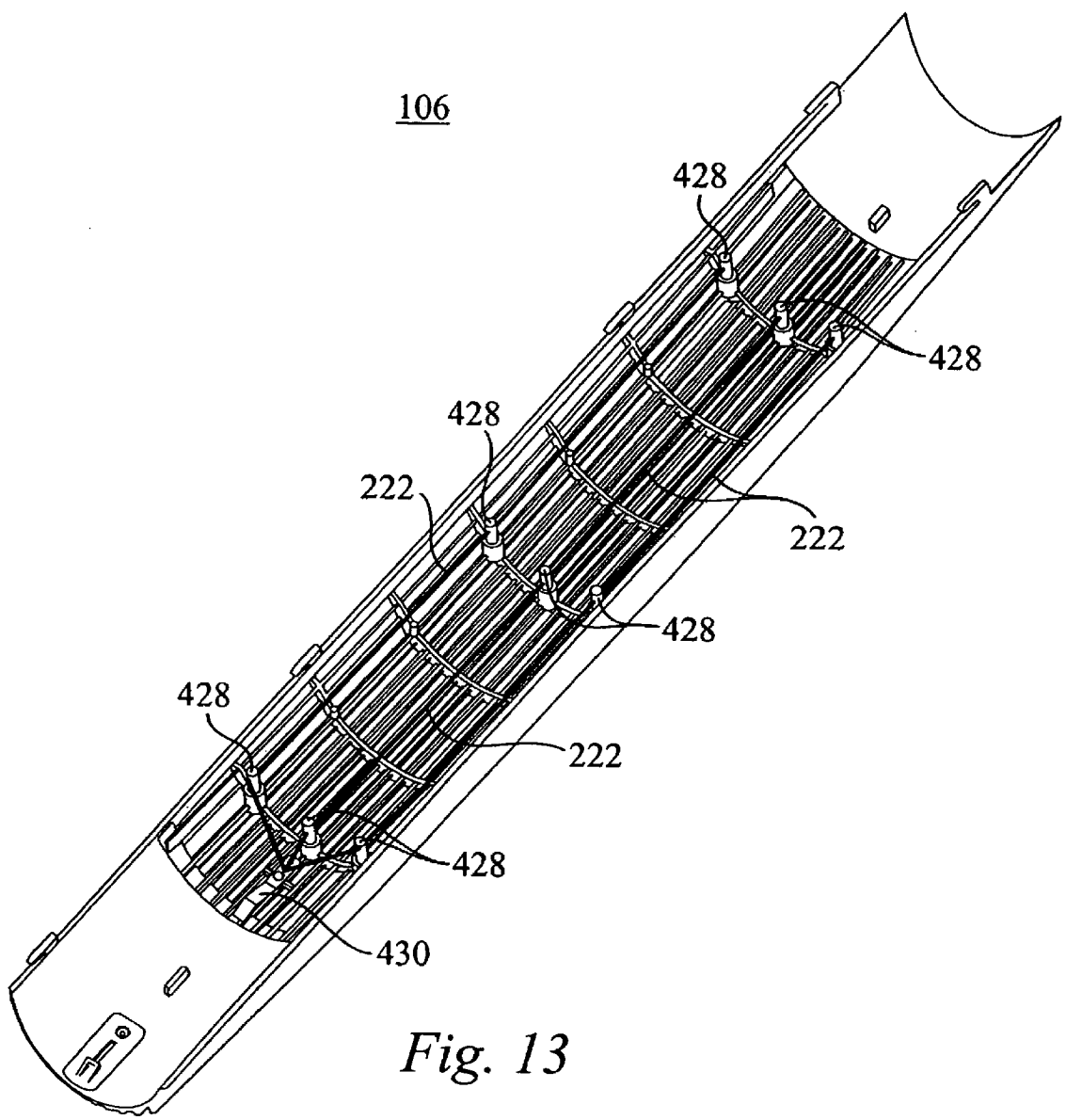
FIG. 13 illustrates a perspective view of the front grill with trailing electrodes thereon in accordance with one embodiment of the present invention.

FIG. 6 illustrates an exploded view of the system 100 in accordance with one embodiment. In particular, FIG. 6 illustrates the housing 102, a rear intake grill 104 (also referred to as inlet), a front exhaust grill 106 (also referred to outlet), collector electrodes 242, driver electrodes 246 and a germicidal lamp 290. The system 100 can also include one or more trailing electrodes 222 (FIG. 13). As shown in the embodiment of FIG. 6, the upper surface of housing 102 can include a handle member 113 that can be lifted by a user to lift the collector electrodes 242 from the housing 102. In the embodiment shown of FIG. 6, the handle member 113 can lift the collector electrodes 242 upward, thereby causing the collector electrodes 242 to telescope out of the aperture 117 in the top 124 of the housing 102 and, if desired, out of the system 100 for cleaning. Additionally, the driver electrodes 246 can be removable from the housing 102 horizontally, as shown in FIG. 6, when the exhaust grill 106 is removed from the housing 102. Alternatively or additionally, the driver electrodes 246 can be removable vertically from the housing 102 as further discussed in U.S. Patent Application No. 60/590,688, which is hereby incorporated by reference in its entirety.

In one embodiment, the housing 102 can be made from a lightweight inexpensive material such as, for example, ABS plastic. Because a germicidal lamp 290 may be located within the housing 102, the material will preferably be able to withstand prolonged exposure to light having germicidal characteristics, such as class UV-C light. Non-"hardened" material can degenerate over time if exposed to light such as UV-C. For example, the housing 102 can be manufactured from CYCLOLAC7 ABS Resin (material designation VW300 (f2)), which is manufactured by General Electric Plastics Global Products and is certified by UL Inc. for use with ultraviolet light. It is within the scope of the present invention to manufacture the housing 102 from other ultraviolet-appropriate materials, as desired.

Figure 7:
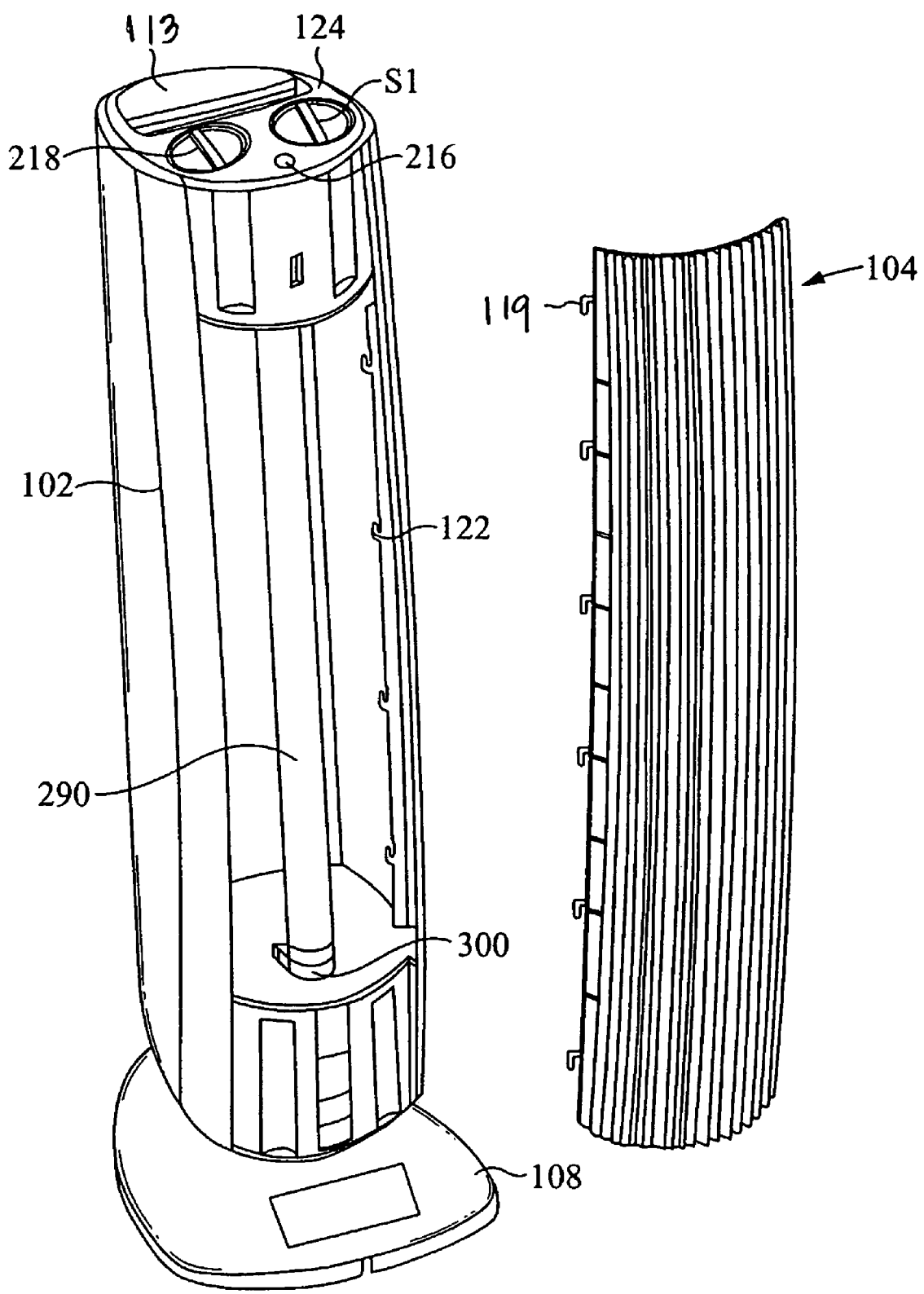
FIG. 7 illustrates a perspective view of the rear of the system with a germicidal lamp exposed in accordance with one embodiment of the present invention.

FIG. 7 illustrates a rear perspective view of the system 100 with the intake grill 104 removed from the housing 102. In one embodiment, the removable intake grill 104 can allow a user to remove easily and replace the germicidal lamp 290 from the receptacle 300 in the housing 102 when the germicidal lamp 290 expires. In the embodiment in which the intake grill 104 is removable, the intake grill 104 can have locking tabs 119 located on each side along the entire length of the intake grill 104. The locking tabs 119, as shown in FIG. 7, can be "L"-shaped. In one embodiment, each locking tab 119 can extend away from the intake grill 104 inward toward the housing 102 and can project downward, parallel with the edge of the intake grill 104. It is also within the scope of the invention to have differently-shaped locking tabs 119. In one embodiment, each locking tab 119 can individually and slidably interlock with recesses 122 formed within the housing 102. The intake grill 104 can be slid vertically upward until the locking tabs 119 disengage the recesses 122. The intake grill 104 can then be pulled away from the housing 102 in a lateral direction, as shown in FIG. 7. Removing the intake grill 104 can expose the germicidal lamp 290 within the housing 102. In one embodiment, the intake grill 104 can include a safety mechanism such as, for example, a rear projecting tab that can be removed from a receiving slot, to shut the system 100 off when the intake grill 104 is removed.

In another embodiment, the germicidal lamp 290 can be removed from the housing 102 by vertically lifting the germicidal lamp 290 out through the top 124 of the housing 102. In one embodiment, the germicidal lamp 290 can be mounted to a lamp fixture that has circuit contacts that engage the circuit 320 (FIG. 4) such that the germicidal lamp 290 can shut the entire system 100 off when lifted out of the housing 102. In a similar but less convenient fashion, the germicidal lamp 290 can be designed to be removed from the bottom of the housing 102 according to known methods.

Figure 8:
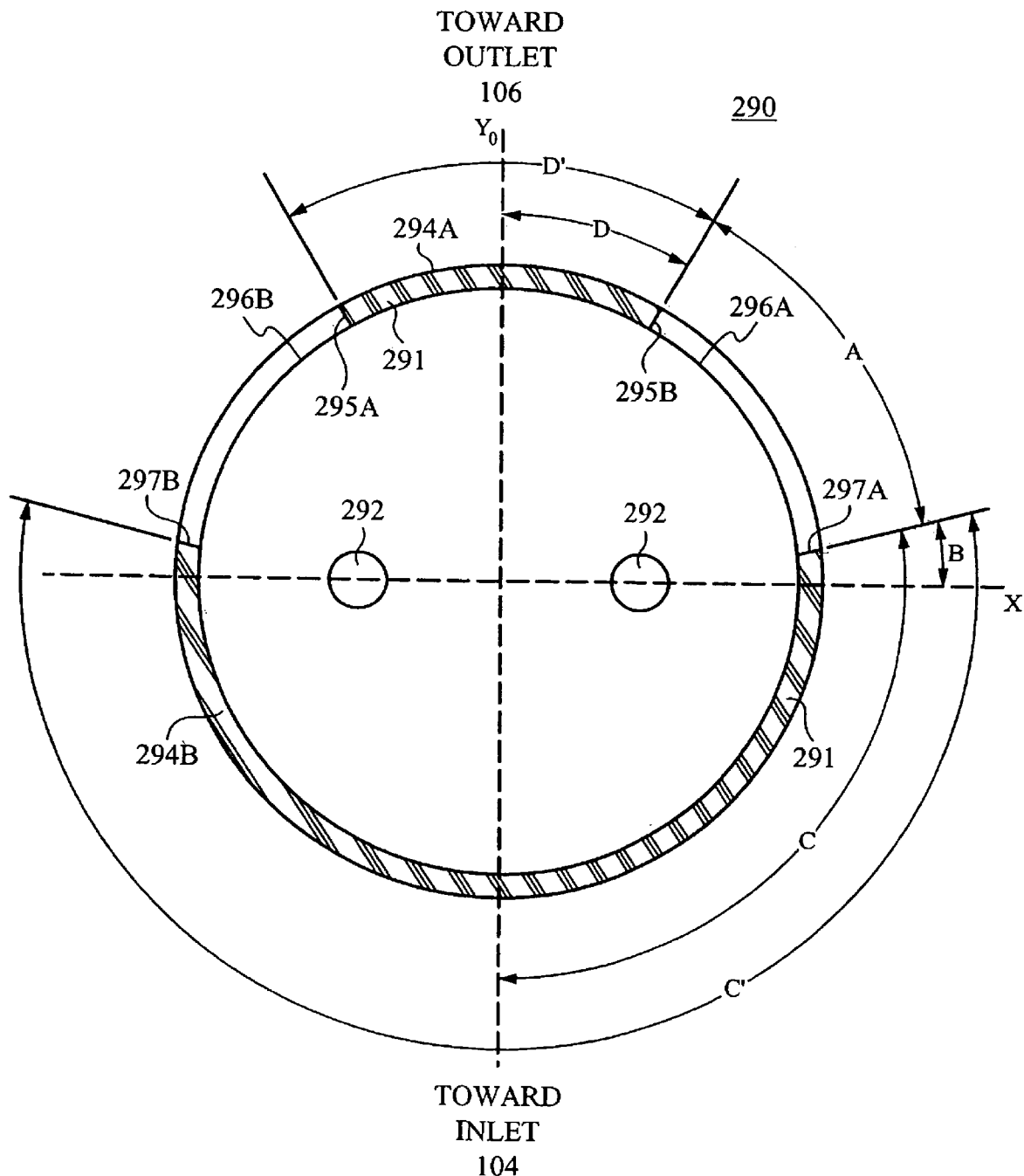
FIG. 8 illustrates a top view of the germicidal lamp in accordance with one embodiment of the present invention.

FIG. 8 illustrates a plan view of one embodiment of the germicidal lamp 290. As shown in FIG. 8, the ends of the germicidal lamp 290 can include two lamp pins 292, which electrically connect the germicidal lamp 290 to the electronic ballast 112 (FIG. 5). However, as discussed below, one or more ends of the germicidal lamp 290 can, alternatively, have additional pins.

Any germicidal lamp 290 that can reduce the viability of microorganisms can be used in the present invention. For example, UV-C lamp having a wavelength of approximately 254 nm, which can be effective in diminishing or destroying bacteria, mold, and viruses to which it is exposed. As shown in FIG. 8, the germicidal lamp 290 can include a shield 294, which selectively directs germicidal light and radiation emitted by the germicidal lamp 290. Many suitable germicidal lamps 290 are known and can be used. For example, the germicidal lamp 290 can be a 15 W tubular lamp measuring approximately 25 mm in diameter by approximately 43 cm in length. It is to be understood that, although the lamp shown and described herein can be applied in a housing with a fan or within an air conditioner system, the germicidal lamp 290 can also be applied in any other application, system or device within the scope of the present invention.

In one embodiment, the germicidal lamp 290 shown in FIG. 8 can include distinct shielded regions 294 and non-shielded regions 296. In one embodiment, the shielded regions 294 of the germicidal lamp 290 can be coated with a shielding material 291, which can prevent germicidal light and radiation emitted by the germicidal lamp 290 from passing therethrough. In one embodiment, the shielding material 291 can be a coating disposed on the inner and/or outer surface of the germicidal lamp 290. In another embodiment, the shielding material 291 can be included in the housing of the germicidal lamp 290. In one embodiment, the shielding material 219 can be formed between the inner and outer surfaces of the germicidal lamp 290. Alternatively, in another embodiment, the shielding material 219 can be formed between and can include the inner and outer surfaces of the germicidal lamp 290. The shielding material 291 of the germicidal lamp 290 can be made of titanium dioxide in one embodiment. However, it is to be understood that the shielding material 291 can be any appropriate material that blocks emission of germicidal light and radiation from the germicidal lamp 290 to the exterior of the housing.

As shown in the Figures, the shielding material 291 can be disposed at predetermined locations of the germicidal lamp 290 such that the shielded regions 294 can face the inlet and outlet, and such that the non-shielded regions 296 can face the inner walls 101 of the housing 102. The shielded regions 294 at which the shielding material 291 is located can depend on the location and orientation of the germicidal lamp 290 within the housing 102, as discussed in more detail below. In one embodiment, the shielded regions 294 can cover the germicidal lamp 290 from the lamp's top end to the lamp's bottom end. Alternatively, in another embodiment, the shielded regions 294 may not be continuous from the top end to the bottom end of the germicidal lamp 290.

As stated above, the non-shielded regions 296 of the germicidal lamp 290 can allow germicidal light and radiation to pass through. In one embodiment, the germicidal lamp 290 can be configured and oriented such that the non-shielded regions 296 can allow germicidal light and radiation to be emitted onto the inner surface 111 of the housing 102 and away from the view of the user. Thus, in this embodiment, the non-shielded regions 296 may not allow germicidal light and radiation to pass directly onto the inlet and outlet of the housing 102. In one embodiment, the germicidal lamp 290 can be oriented such that the shielded regions 294 can face the intake grill 104 and the exhaust grill 106 and, thereby, prevent germicidal light and radiation from being directly emitted toward the inlet and/or outlet so that a user may view the directly emitted light. Additionally, in one embodiment, the configuration of the louvers 134 and placement of the shielded regions 294 can prevent an individual looking into the housing from directly viewing the germicidal light and radiation emitted directly by the germicidal lamp 290. The germicidal lamp 290 of the present invention can, thus, eliminate the need for light deflecting baffles or other housings, which can simplify manufacturing of the system 100. Without such baffles and other housing shields, there is less structure in the housing that can potentially impede the flow of air from the inlet to the outlet. Additionally, the use of the germicidal lamp 290 of the present invention can provide the ability to direct light specifically to a desired location in the housing (e.g., to collector electrodes) if desired.

Figure 9:
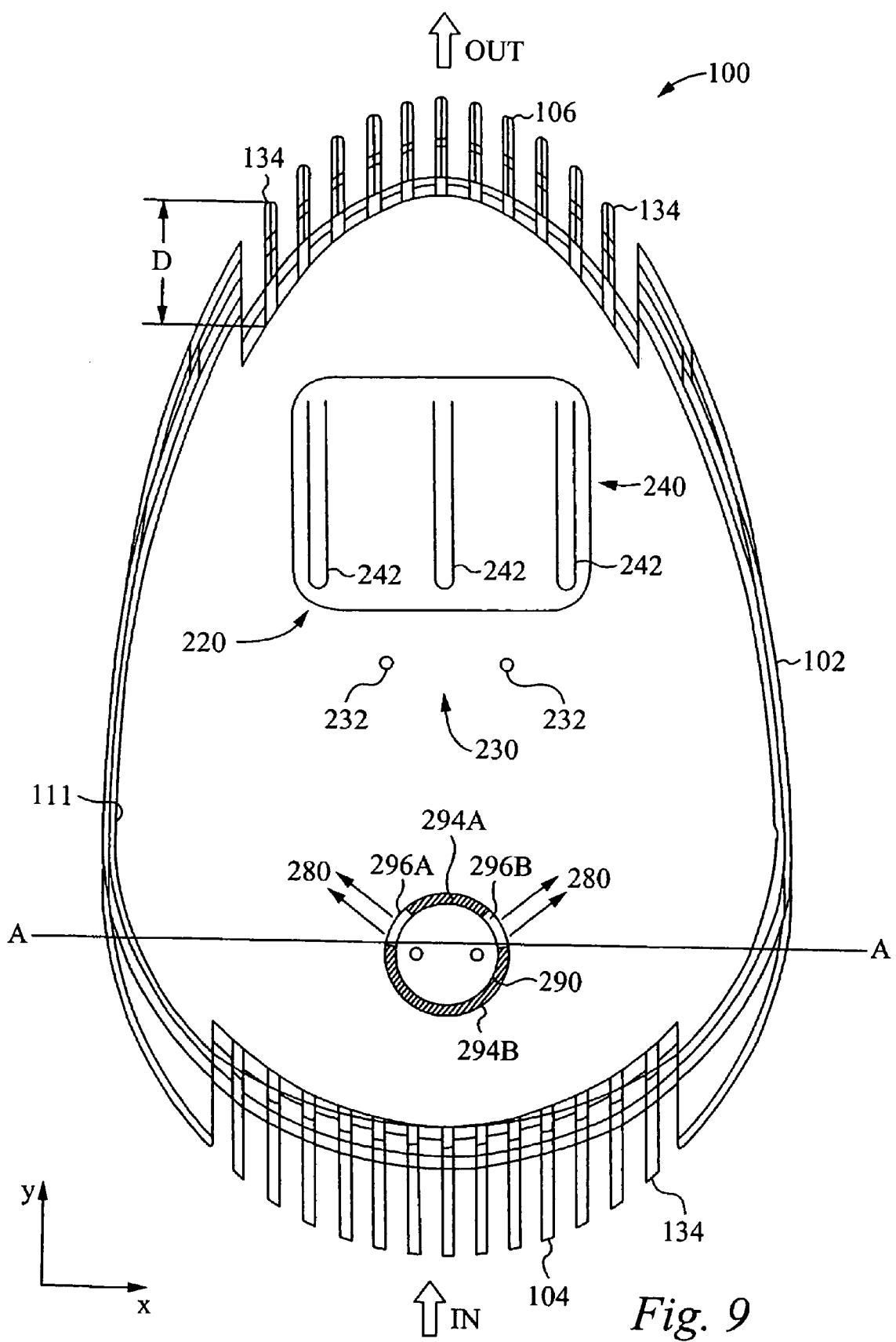
FIGS. 9-11 illustrate the system with the germicidal lamp located at various locations.

As shown in FIG. 9, the system can include an ion generating unit 220 and the germicidal lamp 290 of FIG. 8 located upstream of the ion generating unit 220. In one embodiment, the electrode assembly 220 can be located near the exhaust grill 106, and the germicidal lamp 290 can be located near the intake grill 104 such as, for example, along line A-A. In one embodiment, the germicidal lamp 290 can be placed directly in line with both an intake grill 104 and an exhaust grill 106. In one embodiment, the housing 102 of the present system 100 can be designed to optimize the reduction of microorganisms within the airflow such that the efficacy of radiation 280 upon microorganisms can depend upon the length of time such organisms are subjected to the radiation 280. Thus, in one embodiment, the germicidal lamp 290 can be located within the housing 102 where the airflow is the slowest such as, for example, along line A-A. In one embodiment, line A-A can designate the largest width and cross-sectional area of the housing 102, which can be perpendicular to the airflow. By positioning the germicidal lamp 290 substantially along line A-A, the air may have a long dwell time as it passes through the radiation 280 emitted by the germicidal lamp 290. It is, however, within the scope of the present invention to locate the germicidal lamp 290 anywhere within the housing 102 such as, for example, upstream of the electrode assembly 220

In one embodiment, the inner surface of the housing 102 can be coated with an electrostatic shield to reduce detectable electromagnetic radiation. In one embodiment, a metal shield or metallic paint can be disposed within the housing 102, or regions of the interior of the housing 102. In one embodiment, the inner surface 111 can have a non-smooth finish or a non-light reflecting finish or color. In general, when the germicidal rays emitted by the germicidal lamp 290 strikes the inner surface 111 of the housing 102, the radiation 280 can be shifted from its emitted germicidal spectrum to an appropriate viewable spectrum. Thus, the potentially undesired germicidal portion of the light and radiation 280 that strikes the inner surface 111 can be absorbed by the inner surface 111, whereas the harmless germicidal portion of the radiation 280 can be disbursed as viewable light.

As discussed above, in one embodiment, the louvers 134 covering the intake grill 104 and the exhaust grill 106 can also limit any angle of sight for the individual looking into the housing 102. In one embodiment, the depth D of each fin 134 can be sufficient to prevent an individual from directly viewing the inner surface 111 when looking into the intake and/or exhaust grill 104, 106. Conversely, in one embodiment, the user may be able to "see through" the device upon looking through the inlet and the outlet. It is to be understood that it is acceptable to see light or a glow coming from within the housing 102 if the wavelength of the light renders it acceptable for viewing. Therefore, the configuration of the fins 134 and the germicidal lamp 290 can allow an individual to look into the inlet or the outlet and be able to see light or glow, which may not be harmful to the individual.

Referring back to FIG. 8, specific areas of the germicidal lamp 290 may be configured to include the shielding material 291 such that germicidal light can be directed toward the interior and away from the intake grill 104 and the exhaust grill 106. The germicidal lamp 290 of FIG. 8 is shown placed in the housing 102 of FIG. 9. The specific angles, arc lengths, and locations of the shielded regions 294 and the non-shielded regions 296 of the germicidal lamp 290 are discussed in relation to the Yo axis. In the embodiments of FIGS. 8 and 9, the shielded 294 and non-shielded regions 296 of the germicidal lamp 290 can be symmetrical about the Y axis. As shown in FIGS. 8 and 9, the germicidal lamp 290 can have a front shielded region 294A, which can face the outlet when positioned in the housing 102, and a rear shielded region 294B, which can face the inlet of the housing 102. In one embodiment, a portion of the front shielded region 294A can have an arc-length of approximately 30 degrees clockwise from the Yo axis, shown as angle D, wherein Yo is the reference point of the angles discussed herein. As shown in FIG. 8, the remaining portion of the front shielded region 294A can have an arc length of approximately 30 degrees counterclockwise from the Yo axis (i.e., approximately 330 degrees clockwise with respect to Yo). Thus, for the embodiment shown in FIG. 8, the front shielded region 294A can extend approximately 60 degrees (shown as angle D') from the left end 295A to the right end 295B such that the left end 295A can be approximately 330 degrees from the Yo axis, and the right end 295B can be approximately 30 degrees from the Yo axis. It is to be understood that the angles and arc-lengths discussed above are for one embodiment and are not to be construed to be limited thereto.

The rear shielded region 294B shown in FIG. 8 can extend between a right end 297A and a left end 297B, and can face the inlet of the housing 102. As shown in FIG. 8, the right end 297A of the rear shielded portion 294B can be located approximately 80 degrees from the Yo axis (angle B can be approximately 10 degrees). Additionally, the left end 297B of the rear shielded portion 294B can be located approximately 280 degrees from the Yo axis. Thus, the rear shielded region 294B of the embodiment shown in FIG. 8 can have an arc-length of approximately 100 degrees (angle C) and an overall arc-length of approximately 200 degrees (angle C'). It is to be understood that the angles and arc-lengths discussed above are for one embodiment and are not to be construed to be limited thereto.

In one embodiment, the right non-shielded region 296A of the germicidal lamp 290 can be located adjacent to the front and rear shielded regions 294A, B and can have an arc-length of approximately 50 degrees with respect to the center of the germicidal lamp 290, which is shown as angle A in FIG. 8. Thus, as shown in FIG. 8, the right non-shielded region 296A can extend between the right end 295B of the front shielded region 294A and the right end 297A of the rear shielded region 294B. Because the germicidal lamp 290 can be symmetrical about the Y-axis, the germicidal lamp 290 can also include a left non-shielded region 296B, which can have an arc-length of approximately 50 degrees with respect to the center. The non-shielded region 296 can be located between the left end 295A of the front shielded region 294A and the left end 297B of the rear shielded region 294B in the embodiment shown in FIG. 8. As shown in FIG. 8, the right non-shielded region 296A can have boundaries approximately 30 degrees clockwise from the Y axis (adjacent to front shielded region 294A) and approximately 80 degrees clockwise from the Y axis (adjacent to rear shielded region 294B). As stated above, the germicidal lamp 290 in FIG. 8 can be symmetrical about the Y axis. Therefore, the boundaries of the left non-shielded region 296B can be located approximately 30 degrees counter clockwise from the Y axis (adjacent to the front shielded region 294A) and approximately 80 degrees counter clockwise with respect to the Y axis (adjacent to the rear shielded region 294B). As stated above, it is to be understood that the angles, locations and numbers of shielded and non-shielded regions discussed in relation to FIG. 8 are examples and are not meant to be limiting. Also, it is to be understood that any other angles, locations and numbers of the shielded and non-shielded regions can be used with the present invention.

In one embodiment, the particular angles and locations of the shielded regions 294 and the non-shielded regions 296 can control the location and amount of germicidal light and radiation 280 disbursed by the germicidal lamp 290 within the housing 102. In one embodiment, the front shielded region 294A can be located to face the exhaust grill 106 such that the angle of the front shielded region 294A (i.e., angle D) can radially cover the germicidal lamp 290 and can prevent undesirable germicidal light from being dispersed directly at the exhaust grill 106. Additionally, the rear shielded region 294B can be located to face the intake grill 104 such that the angle of the rear shielded region 294B (i.e., angle C) can radially cover the germicidal lamp 290 and can prevent undesirable germicidal light from being dispersed directly at the intake grill 104. In one embodiment, the non-shielded regions 296A and 296B can be oriented to face the inner walls 101 of the housing and away from the intake and exhaust grill 104, 106 such that an individual looking into the system 100 through the inlet or outlet would not be able to view germicidal light directly emitted by the germicidal lamp 290. In one embodiment, the angles of the non-shielded regions 296 (i.e., angle A) can allow sufficient germicidal light to be emitted out of the germicidal lamp 290 to neutralize microorganisms in the airflow adequately.

Figure 10:
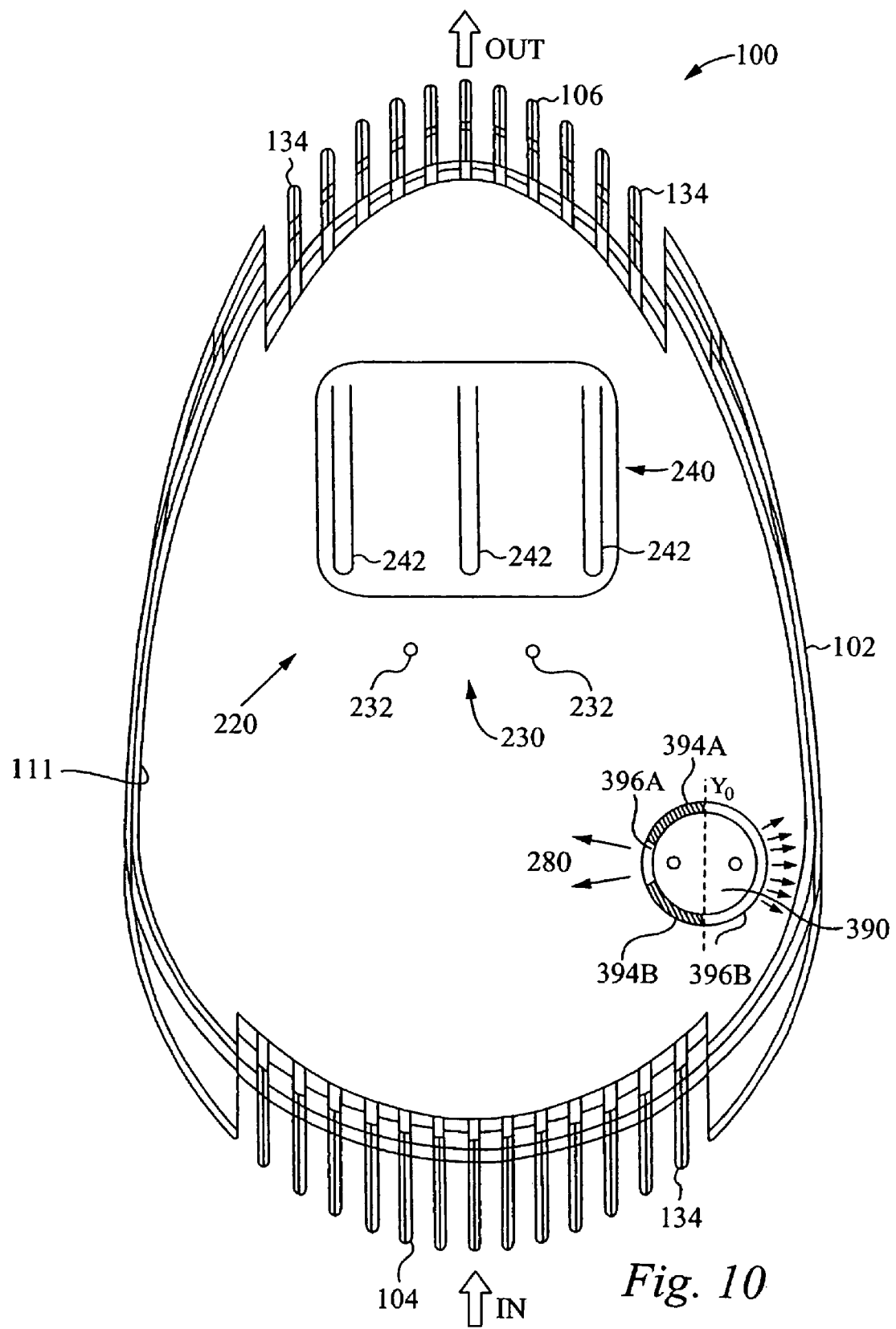

In the embodiment shown in FIG. 10, the germicidal lamp 390 can be located along the side of the housing 102. As the air enters the housing 102, the air can be exposed to the light 280 emitted by the germicidal lamp 390. In FIG. 10, the germicidal lamp 390 can be configured and oriented such that the shielded regions 394A, 394B can block germicidal light 280 from being directed toward the intake grill 104 and exhaust grill 106. In one embodiment, the shape and depth D of the louvers 134 can prevent an individual from seeing the germicidal lamp 390 at an angle into the housing 102. Thus, the front shielded region 394A can cover the portion of the germicidal lamp 390 that can be viewed by an individual looking into the housing 102 through the space between the louvers 134 in the outlet 106. Similarly, in one embodiment, the rear shielded region 394B can shield light emitted from the germicidal lamp 390 from being emitted or viewed through the space between the louvers 134 in the inlet 104.

In one embodiment, the non-shielded regions 396 of the germicidal lamp 390 can be located to face the inner walls 111 of the housing 102. In particular, the non-shielded region 396A (approximately 50 degrees arc length) can be oriented and can have an appropriate radial width to direct light toward the inner wall 111 on the left side of the housing 102 such that undesired germicidal light from the germicidal lamp 390 cannot be viewed by an individual looking into the housing 102. Similarly, in one embodiment, the non-shielded region 396B (approximately 160 degrees in arc-length) can be oriented and can have an appropriate radial width to direct light toward the inner wall 111 on the right side of the housing 102. As shown in FIG. 10, a substantial portion 396B of the germicidal lamp 390 can be out of the direct line of sight through the inlet 104 and the outlet 106, and the portion 396B can be located near the right side of the housing 102. The portion 396B may not be shielded since almost all the light and radiation 280 emitted through the non-shielded portion 396B can be directed onto the inner wall 111 on the right side of the housing 102. In one embodiment, one non-shielded region 396 of the germicidal lamp 390 can face several light guides, which can further prevent the light 280 from shining directly toward the inlet 104 and the outlet 106, and which can also guide the light toward the opposing wall 111. Details of the light guides are described in the U.S. application Ser. No. 10/074,347 which is hereby incorporated by reference in its entirety. It is to be understood that the angles, locations and numbers of shielded and non-shielded regions discussed in relation to FIG. 10 are examples, and are not meant to be limiting. It is also to be understood that any other angles, locations and numbers of the shielded and non-shielded regions can be used with the present invention.

Figure 11:
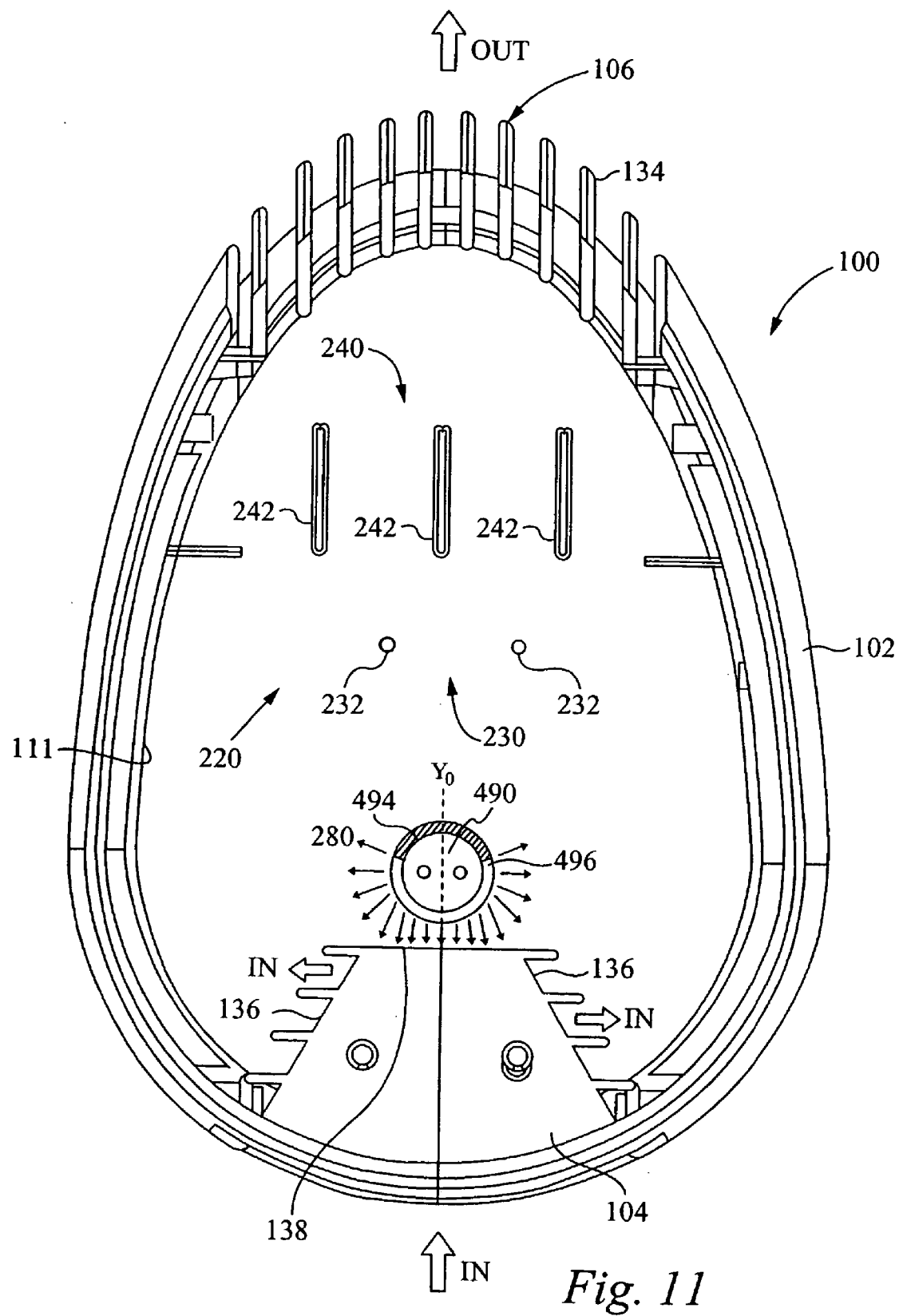

As shown in FIG. 11, the intake grill 104 can include multiple vertical slots 136 located along each side of a rear wall 138 such that the slots 136 can face in a direction perpendicular to the louvers 134 of the exhaust grill 106 and the general direction of the airflow through the system 100. Thus, in this embodiment, air outside of the housing 102 can travel in toward the intake grill 104 and can enter the housing 102 in a perpendicular direction. In one embodiment, the rear wall 138 can be a solid, opaque structure that may not allow light to pass through it. In one embodiment, the rear wall 138 of the intake grill 104 can be coated with the same material as the rest of the interior 111 of the housing and can absorb and/or disburse the germicidal light emitted by the germicidal lamp 490. The germicidal lamp 490 in the embodiment of FIG. 11 can have only one shielded region 494, which can cover a substantial portion of the radial surface of the germicidal lamp 490 that faces the exhaust grill 106. In one embodiment, the shielded region 494 can have an arc-length of approximately 70 degrees with respect to the center, which is similar to the germicidal lamp 290 discussed in FIG. 8. Since, in one embodiment, the rear wall 138 may not allow light to pass through and can have the inlet slots 136 facing perpendicular to the outlet 106 and toward the inner walls 111 of the housing, an individual may not be able to see the non-shielded region of the germicidal lamp 490 by looking into the housing 102 through the inlet slots 136. Thus, in this embodiment, the side of the germicidal lamp 490 that faces toward the inlet 106 may not be shielded. In one embodiment, the germicidal light can be emitted through the non-shielded region and can shine toward the inner wall 111 of the housing 102 and the rear wall 138 of the inlet 104. Nonetheless, in this embodiment, an individual may not be exposed to undesired germicidal rays because the non-shielded region 496 may not be viewable from the outlet 106. It is to be understood that the angles, locations and numbers of shielded and non-shielded regions discussed in relation to FIG. 11 are examples and are not meant to be limiting. Also, it is to be understood that any other angles, locations and numbers of the shielded and non-shielded regions can be used with the present invention.

It is to be understood that the lamp can be used in other air movement devices not specifically mentioned herein. For example, the lamp can be used in an electrostatic precipitator system described in the U.S. patent application Ser. No. 10/774,759, which is hereby incorporated by reference in its entirety. Additionally, the values provided above for the angles and arc-lengths of the shielded and non-shielded regions are examples and should not be limited thereto. Thus, other angles and arc-lengths of the shielded and non-shielded regions can be used with the present invention.

As stated above, the lamp can have shielded and non-shielded regions that can be oriented properly within the housing 102 to prevent undesired germicidal rays from being directed at the inlet 104 and outlet 106. FIGS. 12A and 12B illustrate plan views of the germicidal lamp 290 and receptacle 300 in accordance with one embodiment. As stated above, the germicidal lamp 290 can couple to a lamp holding receptacle 300 such that the germicidal lamp 290 can be selectively removable from the receptacle 300. In one embodiment, the system 100 can include two receptacles 300, wherein each receptacle can engage an end of the germicidal lamp 290. In one embodiment, the germicidal lamp 290 and/or receptacle 300 can be designed such that the germicidal lamp 290 can engage the receptacle 300 in only one manner to ensure that the germicidal lamp 290 can be oriented properly within the housing 102.

As shown in FIG. 12A, the receptacle housing 300 can include an outer receptacle 310 and an inner receptacle 306 located within the outer receptacle 310. In one embodiment, the outer receptacle 310 can be stationary and mounted to the interior of the housing 102, whereas the inner receptacle 306 can be rotatable about its center in the outer receptacle 310. In one embodiment, the inner receptacle 306 can be rotated clockwise to a locked position (FIG. 12B). In contrast, in another embodiment, the inner receptacle 306 can be rotated counterclockwise to an unlocked position (FIG. 12A). In one embodiment, the germicidal lamp 290 can be inserted and removed from the receptacle housing 300 through the opening 308 in the outer receptacle 310.

The germicidal lamp 290 of FIG. 12A can include the two lamp pins 292 and an additional third pin 298, which can extend from the end of the germicidal lamp 290. Although in one embodiment, the lamp pins 292 can be aligned along the center at the end of the germicidal lamp 290, the third pin 298 can be slightly off-center and adjacent to the lamp pins 292. In one embodiment, the inner receptacle 306 can include a first recess 302, which can receive the two lamp pins 292 and a second recess 304, which can be slightly off-center to receive the off-center third pin 298 of the lamp 290. In this embodiment, the offset second recess 304 can force the germicidal lamp 290 to be inserted properly in the housing, thereby ensuring that the user can properly orient the germicidal lamp 290 when engaging the germicidal lamp 290 in the receptacle 300. Upon properly inserting the pins 292, 298 into their respective recesses 302, 304, the germicidal lamp 290 can be rotated clockwise approximately 90 degrees to lock the germicidal lamp 290, as shown in FIG. 12B. The germicidal lamp 290 can be oriented in the manner shown in FIG. 9 when in the locked position. In one embodiment, the lamp pins 292 can come into electrical connect with the voltage source when in the secured position, as shown in FIG. 12B. In one embodiment, removal of the germicidal lamp 290 can be performed in the opposite manner as that described above. In one embodiment, only one of the opposed receptacles 300 can include the second recess 304 to ensure that the germicidal lamp 290 cannot be inserted upside down. However, it is to be understood that both receptacles 300 can have the design described in FIGS. 12A and 12B.

Figure 12C:
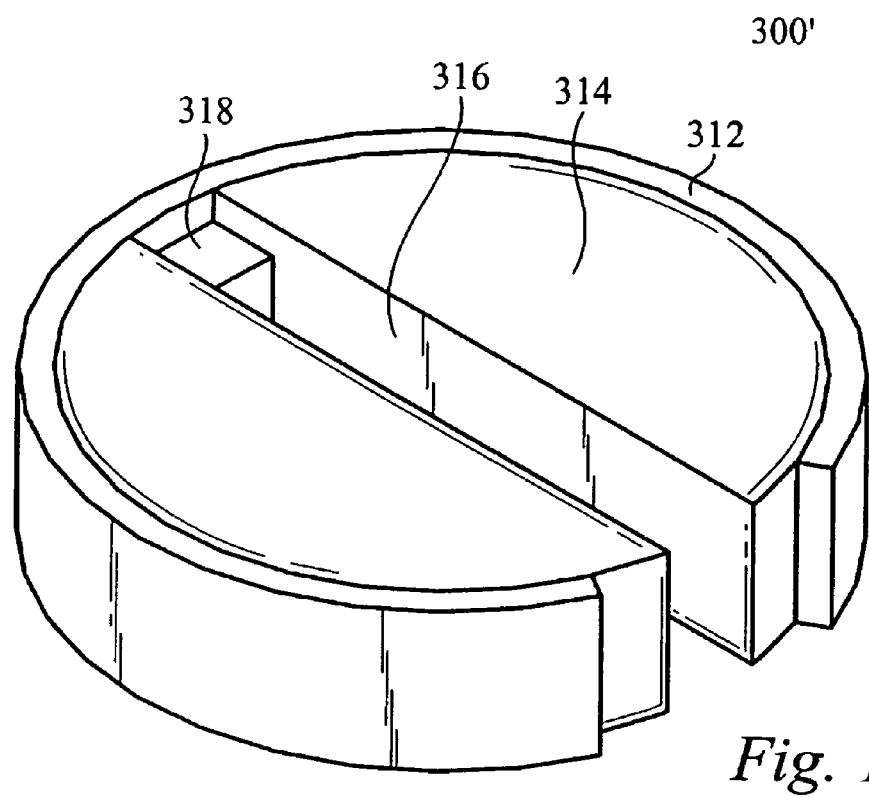
FIG. 12C illustrates a perspective view of the engaging receptacle in accordance with one embodiment of the present invention.
Figure 12D:
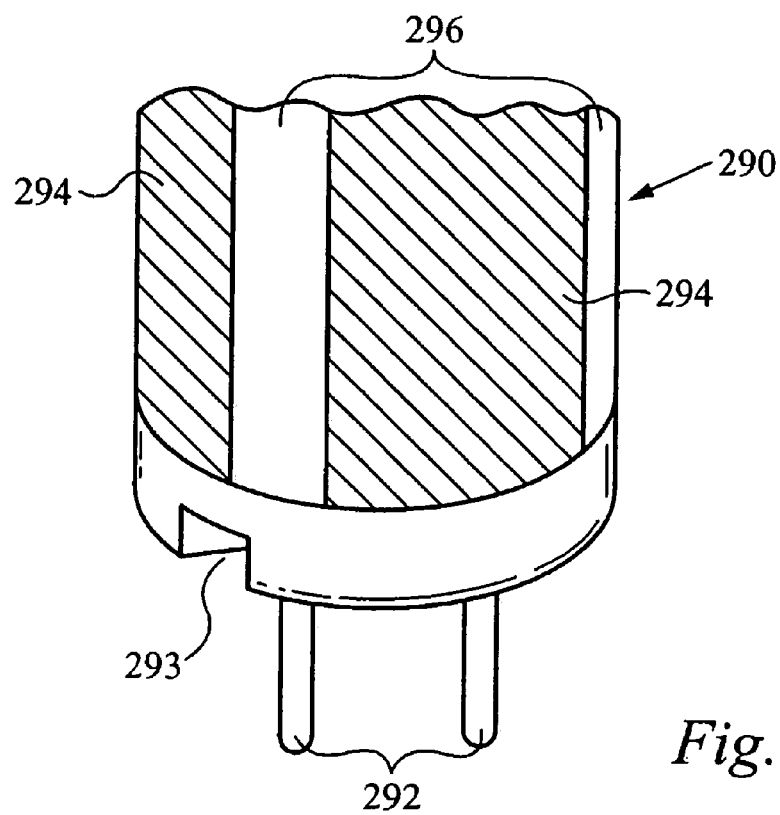
FIG. 12D illustrates a perspective view of the germicidal lamp in accordance with one embodiment of the present invention.

It is to be understood that the above is only one example of how the germicidal lamp 290 and receptacle 300 can be configured and is not to be limited thereto. For example, FIG. 12C illustrates another embodiment of the receptacle housing 300' in which the housing 300' can include the outer receptacle 312 and the rotatable inner receptacle 314. In one embodiment, the receptacle housing 300' can be configured to receive the germicidal lamp 290' shown in FIG. 12D. In one embodiment, the germicidal lamp 290' can include a recess 293 in line with the pins 292 on only one side of the germicidal lamp 290'. In the embodiment shown in FIG. 12C, the rotatable inner receptacle 314 can include one recess 316 which can receive the two pins 292 of the 1 germicidal amp 290'. In one embodiment, a protrusion 318 that can mate with the detent 293 (FIG. 12D) of the germicidal lamp 290 when the detent 293 end of the germicidal lamp 290 is inserted first into the receptacle 300' can also be located within the recess 316. For example, if the non-detent side of the end of the germicidal lamp 290 is inserted into the receptacle first, the germicidal lamp 290' may not be able to be inserted completely into the receptacle 300. It is to be understood that any alternative design can be used to ensure that the germicidal lamp 290 can operate in the system 100 in the proper orientation such that germicidal light directly emitted from the germicidal lamp 290 may not exit or be viewed through the intake and/or exhaust grills 104, 106.

FIG. 13 illustrates a perspective view of the front grill with trailing electrodes thereon in accordance with one embodiment of the present invention. As shown in FIG. 13, the trailing electrodes 222 can be coupled to an inner surface of the exhaust grill 106. This arrangement can allow the user to clean the trailing electrodes 222 from the housing 102 by removing the exhaust grill 106. In one embodiment, placement of the trailing electrodes 222 along the inner surface of the exhaust grill 106 can allow the trailing electrodes 222 to emit ions directly out of the system 100 with a low amount of airflow resistance. Details regarding cleaning of the trailing electrodes 222 are described in U.S. Patent Application No. 60/590,735 which is hereby incorporated by reference in its entirety.

The operation of replacing the germicidal lamp 290 and cleaning the electrodes of the present system 100 will now be discussed. In one embodiment, the intake grill 104 can be removed from the housing 102 first. This can be done by lifting the intake grill 104 vertically and then pulling the intake grill 104 horizontally away from the housing 102, as discussed above in relation to FIG. 7. In one embodiment, the exhaust grill 106 can be removed from the housing 102 in the same manner. In one embodiment, once the intake grill 104 is removed from the housing 102, the germicidal lamp 290 can be exposed. In one embodiment, the user can remove the germicidal lamp 290 by twisting the lamp 290 in a predetermined direction to unlock the 1 germicidal amp 290 from the lamp receptacle 300. Once unlocked, the user can pull the germicidal lamp 290 laterally outward from within the housing 102. In this embodiment, the user can then couple a replacement lamp 290 to the housing 102 by inserting the germicidal lamp 290 into the receptacle 300 in the correct manner discussed above. Upon locking the germicidal lamp 290 within the housing 102, the intake grill 104 can be coupled to the housing 102 in a manner opposite to the intake grill 104 removal process.

In one embodiment, the user can clean the trailing electrodes 222 on the interior of the exhaust grill 106 (FIG. 13). In one embodiment, the user can clean the collector and driver electrodes 242, 246 while the collector and driver electrodes 242, 246 are located within the housing 102. In another embodiment, the user can pull the collector electrodes 242 telescopically out through an aperture 117 in the top 124 of the housing 102, as shown in FIG. 6. In one embodiment, the driver electrodes 246 can be removed from the housing 102 along with the collector electrodes 242. In another embodiment, the driver electrodes 246 can be removed laterally from the housing 102, either along with removal of the exhaust grill 106 or independently of the removal of the exhaust grill 106. Upon removing the collector and driver electrodes 242, 246, the user can clean the electrodes 242, 246 by wiping them with a cloth. Once the collector and driver electrodes 242, 246 are cleaned, the user can insert the collector and driver electrodes 242, 246 back into the housing 102 in a manner opposite to the removal of the electrodes 242, 246. Details regarding the insertion and removal of the driver electrodes 246 and collector electrodes 242 are discussed in the 60/590,688 and 60/590,960 applications, which are hereby incorporated by reference in their entirety.

The foregoing description of the above embodiments of the present invention has been provided for the purposes of illustration and description. It is not intended to be exhaustive or to limit the invention to the precise forms disclosed. Many modifications and variations will be apparent to one of ordinary skill in the relevant arts. The embodiments were chosen and described to explain the principles of the invention and its practical application, thereby enabling others skilled in the art to understand the invention for various embodiments and with various modifications that are suited to the particular use contemplated. It is intended that the scope of the invention be defined by the claims and their equivalence.

It is to be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. An air sanitizing device adapted to neutralize microorganisms comprising:
  a housing having a baffle system through which air can pass and a light shielding system to block germicidal light from exiting the system, wherein the housing includes a removable rear-located air intake grill and a removable front-located air exhaust grill;
  an electrokinetic ion generating device located within the housing for ionizing air, wherein the electrokinetic ion generating device includes:
    a plurality of emitter electrodes,
    a plurality of collector electrodes located downstream from the emitter electrodes;
    a plurality of trailing electrodes located downstream from the collector electrodes for emitting negative ions that neutralize positive ions in the airflow,
    wherein the trailing electrodes are coupled to the air exhaust grill in order to emit negative ions directly out of the housing with low airflow resistance and to be removed from the housing together with the air exhaust grill for cleaning of the trailing electrodes;
  a germicidal lamp located within the housing for irradiating air with germicidal light; and
  a fan located within the housing to draw ambient air into and through the system such that the viability of microorganisms passing through the system is reduced.

2. The air sanitizing device of claim 1, wherein the germicidal lamp is configured to emit radiation in the interior of the housing.

3. The air sanitizing device of claim 1, wherein a region of the germicidal lamp is coated with a shielding material to block emission of ultraviolet light and radiation at the shielded region.

4. The air sanitizing device of claim 1, wherein the shielding system comprises titanium dioxide.

5. The air sanitizing device of claim 1, wherein the germicidal lamp is disposed next to the air intake grill of the housing.

6. The air sanitizing device of claim 1, wherein the electrokinetic ion generating device comprising a plurality of driver electrodes disposed within the housing and located adjacent the collector electrodes, wherein the driver electrode is configured to deflect the particulate matter in the ionized air toward the adjacent collector electrodes.

7. The air sanitizing device of claim 6, wherein at least one of the plurality of emitter electrodes, the plurality of collector electrodes, the plurality of driver electrodes, the plurality of trailing electrodes or the germicidal lamp is removable from the housing.

8. The air sanitizing device of claim 1, wherein the baffle system comprises a plurality of vents configured to block a view of the germicidal lamp.

9. The air sanitizing device of claim 1, wherein the housing comprises a removable top portion containing controls for operation of the device.

10. The air sanitizing device of claim 1, wherein the device further comprises a timing circuit configured to provide an indication of when the germicidal lamp should be replaced.

11. The air sanitizing device of claim 1, wherein the germicidal lamp is an ultraviolet lamp.

12. The air sanitizing device of claim 1, wherein the amount of negative ions emitted by the trailing electrodes is controlled by varying voltage supplied to the trailing electrodes independently from voltage supplied to the emitter and collector electrodes.

13. The air sanitizing device of claim 1, wherein the trailing electrodes operate at a different duty cycle, amplitude, pulse width, and frequency than the emitter and collector electrodes.

14. The air sanitizing device of claim 1, wherein the amount of negative ions emitted by the trailing electrodes and the duration of time for which ions are emitted by the trailing electrodes are manually controlled by a user of the air sanitizing device.

15. The air sanitizing device of claim 1, wherein the amount of negative ions emitted by the trailing electrodes and the duration of time for which ions are emitted by the trailing electrodes are automatically controlled by the air sanitizing device.

16. An air sanitizing device adapted to neutralize microorganisms comprising:
  a housing having a a removable rear-located air intake grill and a removable front-located air exhaust grill;
  a top portion containing controls for operation of the device;
  an electrokinetic ion generating device located within the housing for ionizing air, wherein the electrokinetic ion generating device includes:
    a plurality of emitter electrodes,
    a plurality of collector electrodes located downstream from the emitter electrodes;

a plurality of trailing electrodes located downstream from the collector electrodes for emitting negative ions that neutralize positive ions in the airflow, wherein the trailing electrodes are coupled to the air exhaust grill in order to emit negative ions directly out of the housing with low airflow resistance and to be removed from the housing together with the air exhaust grill for cleaning of the trailing electrodes;

a germicidal lamp located within the housing for irradiating air with germicidal light; and a fan located within the housing to draw ambient air into and through the system such that the viability of microorganisms passing through the system is reduced.

17. The air sanitizing device of claim 16, further comprising a light shielding system comprising titanium dioxide to block germicidal light from exiting the system.

18. The air sanitizing device of claim 16, wherein the amount of negative ions emitted by the trailing electrodes is controlled by varying voltage supplied to the trailing electrodes independently from voltage supplied to the emitter and collector electrodes.

19. The air sanitizing device of claim 16, wherein the trailing electrodes operate at a different duty cycle, amplitude, pulse width, and frequency than the emitter and collector electrodes.

20. The air sanitizing device of claim 16, wherein the amount of negative ions emitted by the trailing electrodes and the duration of time for which ions are emitted by the trailing electrodes are manually controlled by a user of the air sanitizing device.

21. The air sanitizing device of claim 16, wherein the amount of negative ions emitted by the trailing electrodes and the duration of time for which ions are emitted by the trailing electrodes are automatically controlled by the air sanitizing device.

* * * * *